United States Patent [19]
Itagaki et al.

[11] Patent Number: 5,929,996
[45] Date of Patent: *Jul. 27, 1999

[54] METHOD AND APPARATUS FOR DETECTING MINUTE IRREGULARITIES ON THE SURFACE OF AN OBJECT

[75] Inventors: Chuji Itagaki, Tokyo; Masahiro Itou, Machida; Kouzou Ichiba, Tokyo, all of Japan

[73] Assignee: Toshiba Engineering Corporation, Kawasaki, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/743,799

[22] Filed: Nov. 5, 1996

Related U.S. Application Data

[63] Continuation of application No. 08/329,910, Oct. 27, 1994., abandoned

[30] Foreign Application Priority Data

| Oct. 27, 1993 | [JP] | Japan | P05-268992 |
| Feb. 10, 1994 | [JP] | Japan | P06-016803 |
| Feb. 15, 1994 | [JP] | Japan | P06-039283 |

[51] Int. Cl.$^6$ ................................. G01B 11/24
[52] U.S. Cl. .................. 356/376; 356/237; 356/390; 356/375; 356/429
[58] Field of Search .................... 356/237, 390, 356/392, 394, 375, 429–431; 282/112, 144–149, 141, 143, 170, 205; 250/559.39, 559.41, 559.42, 559.43, 559.45, 559.46, 559.48, 559.29; 348/125–126, 128–130

[56] References Cited

U.S. PATENT DOCUMENTS

| 4,500,202 | 2/1985 | Smyth | 356/237 |
| 4,532,650 | 7/1985 | Wihl et al. | 356/237 |
| 4,667,247 | 5/1987 | Karow | 358/280 |
| 4,679,075 | 7/1987 | Williams et al. | 356/237 |
| 4,692,943 | 9/1987 | Pietzsch et al. | 356/237 |
| 4,701,782 | 10/1987 | Duvent | 358/227 |
| 4,707,734 | 11/1987 | Labinger et al. | 382/8 |
| 4,845,558 | 7/1989 | Tsai et al. | 358/106 |
| 4,881,270 | 11/1989 | Kuecht et al. | 382/191 |
| 5,056,524 | 10/1991 | Oe | 364/413.23 |
| 5,070,413 | 12/1991 | Sullivan et al. | 358/456 |
| 5,073,961 | 12/1991 | Takeo | 382/27 |
| 5,113,454 | 5/1992 | Marcantonio et al. | 356/237 |
| 5,187,376 | 2/1993 | Hashimoto et al. | 250/562 |
| 5,235,985 | 8/1993 | McMorrow et al. | 128/660.07 |
| 5,239,184 | 8/1993 | Mancuso et al. | 250/562 |
| 5,249,034 | 9/1993 | Minato | 356/237 |
| 5,268,968 | 12/1993 | Yoshida | 382/141 |
| 5,374,959 | 12/1994 | Sahakiou | 348/451 |
| 5,513,275 | 4/1996 | Khalaj et al. | 382/149 |

*Primary Examiner*—Robert H. Kim
*Attorney, Agent, or Firm*—Oblon, Spivak, McClelland, Maier & Neustadt, P.C.

[57] ABSTRACT

The present invention provides a method and apparatus of inspecting a surface of an object article capable of precisely detecting stains or miniature defects present in the object surface. Specifically, the invention provides a method of inspecting surface irregularity of an object article having a surface of uniform or regular brightness, which comprises the steps of: gaining brightness informations for a plurality of two-dimensionally distributed pixels by taking a picture of the article surface; finding stains on the article surface in response to each information obtained in the brightness information gaining step to produce a first output; finding miniature defects smaller in size than a unit pixel in response to each information obtained in the brightness information gaining step to generate a second output; switching the first output and the second output into appropriate electrical signals in an controlled manner; and displaying the switched electrical signals on a display in a viewable condition.

11 Claims, 25 Drawing Sheets

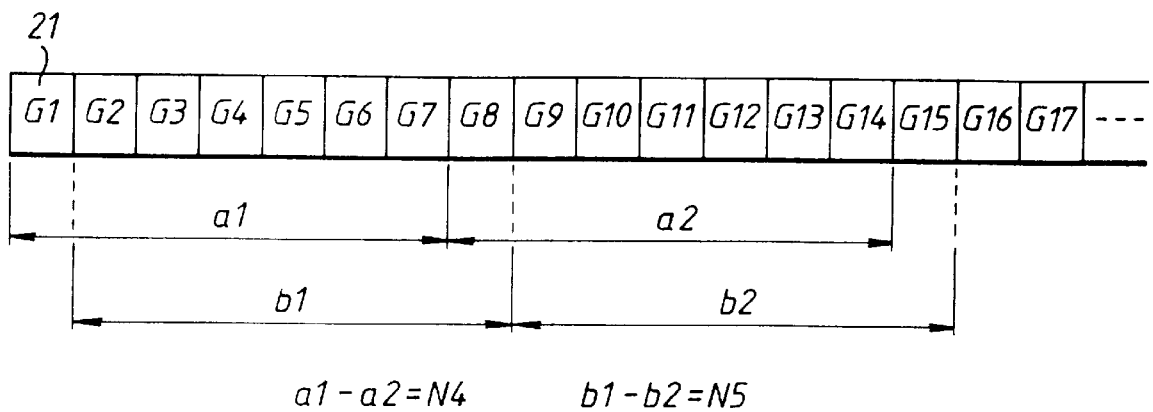
$a1-a2=N4 \qquad b1-b2=N5$
Fig. 2 (PRIOR ART)
Fig. 3(a) (PRIOR ART)
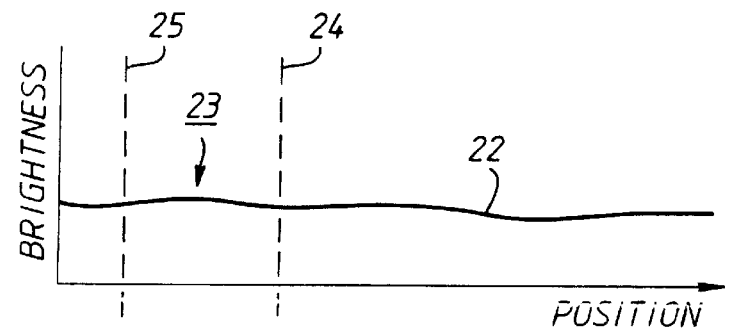
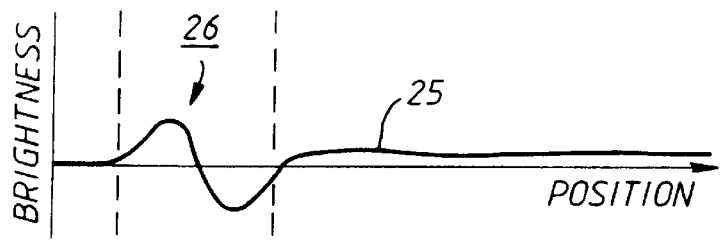
Fig. 3(b) (PRIOR ART)

| -1 | -2 | -1 |
|----|----|----|
| 0  | 0  | 0  |
| 1  | 2  | 1  |

*Fig.17*

| -1 | 0 | 1 |
|----|---|---|
| -2 | 0 | 2 |
| -1 | 0 | 1 |

*Fig.18*

METHOD AND APPARATUS FOR DETECTING MINUTE IRREGULARITIES ON THE SURFACE OF AN OBJECT

This application is a continuation of application Ser. No. 08/329,910, filed on Oct. 27, 1994, now abandoned.

BACKGROUND OF THE INVENTION

1. Field of the Invention

The present invention relates to generally to inspection of irregularity or unsteadiness possibly appearing on the surface of objects, specimens and the like, and more specifically to a method and apparatus for detecting surface irregularity of objects, e.g., less conspicuous spots with imperceptible boundary scattered on an object surface, blot zones of differing density often present on the patternless homogenious surface of monolithic object, flaws on a patternless sheet-like specimen, and positional defects in an array of objects arranged at predetermined pitch. Even more particularly, the instant invention is directed to a method and apparatus capable of examining stains or stain areas, minute flaws and crosswise defects of unclear boundary with no remarkable brightness difference, frequently appearing on the surface of various articles.

2. Description of the Prior Art

As is conventional, in the liquid crystal display hereinafter referred to as "LCD", there occurs an occasion that the color filters thereof partially become bright or dark due mainly to the presence of dyeing stains. Likewise, spots of, e.g., differing density or thickness may be created in case of a monochromic patternless woven fabric attached to the ceiling of motor vehicles or a similar nonwoven fabric patch used as a drug carrier. This holds true for the shadow mask of a color cathode ray tube. Namely, electron beam penetration holes formed through the shadow mask may have irregular configuration or may be distributed in an erroneous spacing or pattern. In addition to the above, minute defects or alien matters are often found in a patternless film or an aluminum sheet for use in making beverage cans.

In accordance with the prior art approach, such a surface irregularity of object articles has been detected through the use of an inspection apparatus that includes a line sensor and an image processor associated therewith. The inspection apparatus is designed to find out surface defects by way of first scanning the surface of the object articles to obtain brightness information for each and every pixel and subsequently determining whether the respective brightness information falls within a permissible range.

As a more specific prior art example, the surface examination device shown in FIG. 1 has been used to detect a stain 2 possibly present on a LCD color filter 1. This device comprises a line sensor 10, an image processor 11 and a display 12 wherein the image processor 11 is, in turn, provided with a plurality of brightness information adders 13, 15, a subtracter 14 and an evaluater 17.

In order to detect the stain as a surface defect by means of the examination device noted above, the line sensor 10 takes a picture of the LCD color filter 1 to gain brightness information G1, G2, G3, . . . and Gn for the respective pixel 21 depicted in FIG. 2. The brightness informations may be graphically represented as in FIG. 3(a) in which the ordinate indicates brightness with the abscissa pixel position. The rising ridge 23 sandwiched between a couple of broken lines 24, 25 in the brightness information curve 22 corresponds to the stain on the LCD color filter 1.

In the next step, it is necessary to select a given number of, e.g., seven pixels G1 through G7, the brightness informations of which are summed by use of the first brightness information adder 13 to gain total brightness value a1. Similarly, the brightness informations for the successive pixels G8 through G14 are summed by use of the second brightness information adder 15 to gain total brightness value a2. The subtracter 14 comes to draw total value a2 from total value a1 in an effort to gain differential data N4. The evaluater 17 will then analyze the differential data N4 to see whether it falls within a permissible range. If the data N4 is determined to fall outside the permissible range, it should be recognized that there would exist a pixel or pixels of irregular brightness among the examined pixels.

In the subsequent step, another group of pixels G2 through G8 shifted rightward by one pixel pitch are selected to sum the brightness informations thereof by use of the first adder 13, thus gaining total brightness value b1. In the same way, the brightness informations for the successive pixels G9 through G15 are summed up by use of the second adder 15 to gain total brightness value b2. The subtracter 14 comes to draw total b2 from total value b1 so as to gain differential data N5.

The above processing is repeatedly performed for the entire pixels with a view to obtaining their differential data. The display 12 plays a part in representing the resultant data in a readily understandable form. FIG. 3(b) is a graphical representation of the differential data obtained through the foregoing process. It can be readily seen that the curve 25 of FIG. 3(b) has a ridge and valley portion 26 sandwiched between the broken lines 24, 25, which is more conspicuous than the ridge 23 of the curve 22 shown in FIG. 3 (a). The same processing as set forth above can be executed in the y-axis direction as noted by an arrow 4 in FIG. 1 in order to two-dimensionally highlight the stain or defect.

The prior art surface defect inspection device exemplified in the foregoing is, however, inherently disadvantageous in terms of the following four aspects.

(1) In case of examining surface defects of an object article with lattice-like pattern as shown in FIG. 4, e.g., LCD color filter 1, the intersection point formed by a detection line 31 of the line sensor 10 and a lattice line 32 of the filter 1 may be erroneously recognized as a surface defect, if there exists a misalignment between the LCD color filter 1 and the detection line 31 of the line sensor 10.

(2) Although it is possible to detect the linear stain 33 extending perpendicular to the detection line 31 of the line sensor 10 as depicted in FIG. 5, this is not the case for the horizontally extending linear stain 34 which is parallel to the detection line 31 of the line sensor 10 as shown in FIG. 6. The reason for the horizontally extending liner stain being undetectable is that there would occur no fluctuation between each of the brightness informations of the horizontal stain.

(3) Lastly, it is a frequent occasion that tiny alien matters or diminutive flaws 62 hereinafter referred to collectively as "miniature defects" may be borne by a sheet-like patternless film or an aluminium sheet for the manufacture of beverage cans, as is apparent from FIG. 7. If the miniature defects 62 have a dimension of less than or slightly greater than the pixel size, it becomes hard to detect the miniature defects by way of solely determining whether the brightness informations for the respective pixel fall within or outside the prescribed range. For the "shading" or high frequency noise 71 would preclude convenient detection of the miniature defects 72, as indicated in FIG. 8.

SUMMARY OF THE INVENTION

Accordingly, it is an object of the present invention to provide a method for inspecting surface irregularity of object articles that makes it possible to detect not only low contrast specks out of an article surface but also miniature defects having a dimension of less than or slightly greater that the size of a sensor pixel. With this object in view, the invention provides a method of inspecting surface irregularity of an object article having a surface of uniform or regular brightness, which comprises the steps of:

gaining brightness informations for a plurality of two-dimensionally distributed pixels by taking a picture of the article surface;

finding stains on the article surface in response to each information obtained in the brightness information gaining step to produce a first output;

finding miniature defects smaller in size than a unit pixel in response to each information obtained in the brightness information gaining step to generate a second output;

switching the first output and the second output to appropriate electrical signals in a controlled manner; and displaying the switched electrical signals on a display in a viewable condition.

Specifically, the stain finding step comprises the substeps of:

dividing the brightness informations for each of the pixels into a plurality of lattices each having a given number of row and column matrixes; adding the brightness informations of the pixels in respective lattice to gain sum brightness values for each of the lattices; calculating magnitudes of fluctuation in the sum brightness values along horizontal and vertical directions with respect to said lattices; and detecting presence to the stains when the fluctuation magnitudes exceed a predetermined value.

The fluctuation magnitude calculating step includes gaining the horizontal and vertical fluctuation magnitudes through the use of first horizontal and second vertical coefficient tables on the basis of N (m rows by n columns) sum brightness values around a reference brightness value for one optional lattice.

Preferably, each of the first horizontal and second perpendicular coefficient tables is a Sobel filter.

The defect finding step comprises the substeps of: calculating magnitudes of fluctuation in each of the brightness informations along horizontal and vertical direction with respect to said lattices; adding the horizontal and vertical fluctuation magnitudes on a pixel basis; averaging the added fluctuation magnitudes on a pixel basis to gain a mean fluctuation magnitude; and detecting presence of the defects when the mean fluctuation magnitude exceeds a predetermined value.

The fluctuation magnitude calculating step includes gaining the horizontal and vertical fluctuation magnitudes through the use of a first coefficient table emphasizing a horizontally extending contour and a second coefficient table emphasizing a vertically extending contour on the basis of N (m rows by n columns) brightness informations around a reference brightness information for one optional pixel. It is preferred that each of the first horizontal and second vertical coefficient tables is a Sobel filter.

The averaging step is performed through the use of a table of m rows by n columns on the basis of N (m rows by n columns) fluctuation magnitudes around a reference fluctuation magnitude for one optional pixel.

Particularly, the stain finding step comprises the substeps of: dividing the brightness informations for each of the pixels into a plurality of lattices each having a given number of row and column matrixes; adding the brightness informations of the pixels in the respective lattice to gain sum brightness values for each of the lattices; calculating magnitudes of fluctuation in the sum brightness values along horizontal and vertical directions; and detecting presence of the stains when the fluctuation magnitudes exceed a predetermined value, and the defect finding step comprises the substeps of: calculating magnitudes of fluctuation in each of the brightness informations along horizontal and vertical direction with respect to said lattices; adding the horizontal and vertical fluctuation magnitudes on a pixel basis; averaging the added fluctuation magnitudes on a pixel basis to gain a mean fluctuation magnitude; and detecting presence of the defect when the mean fluctuation magnitude exceeds a predetermined value.

The fluctuation magnitude calculating step in the stain finding step includes gaining the horizontal and vertical fluctuation magnitudes through the use of first horizontal and second vertical coefficient tables on the basis of N (m rows by n columns) sum brightness values around a reference sum brightness value for one optional lattice.

Desirably, each of the first horizontal and second vertical coefficient tables is a Sobel filter.

In addition, the fluctuation magnitude calculating step includes gaining the horizontal and perpendicular fluctuation magnitudes through the use of a first coefficient table emphasizing a horizontally extending contour and a second coefficient table emphasizing a vertically extending contour on the basis of N (m rows by n columns) brightness informations around a reference brightness information for one optional pixel.

It is desired that each of the first and second coefficient tables is a Sobel filter.

The averaging step is performed through the use of a table of m rows by n columns of the basis of N (m rows by n columns) fluctuation magnitudes around a reference fluctuation magnitude for one optional pixel.

Another object of the present invention is to provide a method and apparatus for inspecting surface irregularity of object articles which has the capability of detecting spots and defects on the object articles with an acceptable accuracy but with no dependency of detection direction.

With this object in view, the invention provides a method of inspecting surface irregularity of an object article to detect specks of unclear boundary and low brightness difference, which comprises the steps of:

gaining brightness informations for a plurality of two-dimensionally distributed pixels by use of an image sensor;

dividing the brightness informations for each of the pixels into a plurality of lattices each having a given number of row and column matrixes;

adding the brightness information of the pixels in the respective lattice to gain sum brightness values for each of the lattices;

calculating magnitudes of fluctuation in the sum brightness values along horizontal and vertical directions with respect to said lattices; and detecting presence of the specks when the fluctuation magnitudes exceed a predetermined value.

The fluctuation magnitude calculating step includes gaining the horizontal and vertical fluctuation magnitudes through the use of first horizontal and second vertical efficient tables on the basis of N (m rows by n columns) sum brightness values around a reference brightness value for one optional lattice.

Further, the invention provides an apparatus of inspecting surface irregularity of an object article to detect specks of unclear boundary and low brightness difference, which comprises:

- a line or area sensor for taking a picture of the article surface to gain brightness informations for a plurality of two-dimensionally distributed pixels;
- a brightness information adder for dividing the brightness informations for each of the pixels into a plurality of lattices each having a given number of row and column matrixes and then for adding the brightness informations of the pixels in the respective lattice to gain sum brightness values for each of the lattices;
- a fluctuation magnitude calculator for calculating magnitudes of fluctuation in the sum brightness values along horizontal and vertical directions; and
- a detector for detecting presence of the specks when the fluctuation magnitudes exceed a predetermined value.

The fluctuation magnitude calculator serves to gain the horizontal and vertical fluctuation magnitudes through the use of first horizontal and second vertical coefficient tables on the basis of N (m rows by n columns) sum brightness values around a reference brightness value for one optional lattice.

In accordance with the apparatus mentioned above, the brightness information adder is adapted to divide the brightness informations for each of the pixels into a plurality of lattices each having a given number of row and column matrixes and to add the brightness informations of the pixels in the respective lattice to gain sum brightness values for each of the lattices, the fluctuation magnitude calculator is adapted to calculate magnitudes of fluctuation in the sum brightness values along horizontal and vertical directions, and the detector is adapted to detect presence of the specks when the fluctuation magnitudes exceed a predetermined value.

A further object of the present invention is to provide a surface irregularity inspection apparatus capable of precisely detecting speck areas of differing density and low contrast out of a monochromic patternless object article by way of emphasizing the speck areas in an image of the object article.

With the object in view, the invention provides an apparatus comprising:

- a sensor, e.g., a line or area sensor for taking a picture of the article surface to gain brightness informations for a plurality of two-dimensionally distributed pixels;
- a brightness information adder means for dividing the brightness informations for each of the pixels into a plurality of lattices each having a given number of row and column matrixes and then for adding the brightness informations of the pixels in the respective lattice to gain sum brightness values for each of the lattices;
- a fluctuation magnitude calculator means for calculating magnitudes of fluctuation in the sum brightness values along horizontal and vertical directions;
- and a detector means for detecting presence of the speck areas when the fluctuation magnitudes exceed a predetermined value.

The fluctuation magnitude calculator means serves to gain the horizontal and vertical fluctuation magnitudes through the use of first horizontal and second vertical coefficient tables on the basis of N (m rows by n columns) sum brightness values around a reference brightness value for one optional lattice.

In accordance with the apparatus described above, the brightness information adder means in adapted to divide the brightness informations for each of the pixels into a plurality of lattices each having a given number of row and column matrixes and to add the brightness informations of the pixels in the respective lattice to gain sum brightness values for each of the lattices, the fluctuation magnitude calculator means is adapted to calculate magnitudes of fluctuation in the sum brightness values along horizontal and vertical directions, and the detector means is adapted to detect presence of the speck areas when the fluctuation magnitudes exceed a predetermined value.

As a result, it becomes possible to emphasize the image of speck areas of differing density present in the monochromic, patternless object article, so that the speck areas of unclear boundary can be detected at a high accuracy.

Further, the fluctuation magnitude calculator means serves to gain the horizontal and vertical fluctuation magnitudes through the use of first horizontal and second vertical coefficient tables on the basis of N (m rows by n columns) sum brightness values around a reference brightness value for one optional lattice.

A still further object of the present invention is to provide a surface irregularity inspection method capable of detecting defects of an object article, e.g., defective electron beam penetration holes of a shadow mask, with acceptable accuracy by way of emphasizing the defects in an image of the object article.

With the object in view, the invention provides a method of inspecting an object area on which a plurality of object elements are arranged at a predetermined pitch, to detect defects present in the object area, comprising the steps of:

- gaining brightness informations for a plurality of two-dimensionally distributed pixels by use of an image sensor;
- dividing, on a pitch basis, the brightness informations for each of the pixels into a plurality of lattices each having a given number of row and column matrixes and then adding the brightness informations of the pixels in the respective lattice to gain sum brightness values for each of the lattices;
- calculating magnitude of fluctuation in the sum brightness values along horizontal and vertical directions; and
- detecting presence of the defects when the fluctuation magnitudes exceed a predetermined value. Preferably, the sensor may be either a line or area sensor.

The fluctuation magnitude calculating step includes gaining the horizontal and vertical fluctuation magnitudes through the use of first horizontal and second vertical coefficient tables on the basis of N (m rows by n columns) sum brightness values around a reference brightness value for one optional lattice.

Further, the invention provides an apparatus of inspecting an object area on which a plurality of object elements are arranged at a predetermined pitch, to detect defects present in the object area, which comprises:

- a sensor for taking a picture of the object area to gain brightness informations for a plurality of two-dimensionally distributed pixels;
- a brightness information adder for dividing, on a pitch basis, the brightness informations for each of the pixels into a plurality of lattices each having a given number of row and column matrixes and then for adding the brightness informations of the pixels in the respective lattice to gain sum brightness values for each of the lattices;
- a fluctuation magnitude calculator for calculating magnitudes of fluctuation in the sum brightness values along horizontal and vertical directions with respect to said lattices;

and a detector for detecting presence of the defects when the fluctuation magnitudes exceed a predetermined value.

The sensor may preferable be either a line or area sensor.

The fluctuation magnitude calculator serves to gain the horizontal and vertical fluctuation magnitudes through the use of first horizontal and second vertical coefficient tables on the basis of N (m rows by n columns) sum brightness values around a reference brightness value for one optional lattice.

In accordance with the apparatus mentioned above, the brightness information adder is adapted to divide the brightness informations for each of the pixels into a plurality of lattices each having a given number of row and column matrixes and then to add the brightness informations of the pixels in the respective lattice to gain sum brightness values for each of the lattices, the fluctuation magnitude calculator is adapted to calculate magnitudes of fluctuation in the sum brightness values along horizontal and vertical directions, and the detector is adapted to detect presence of the defects when the fluctuation magnitudes exceed a predetermined value.

A yet still further object of the present invention is to provide surface irregularity inspections method and apparatus which have the ability to precisely detect miniature defects appearing on the surface of an object article.

With the object in view, the invention provides an apparatus of inspecting surface irregularity of an object article, which comprises:

a sensor, e.g., a line or area sensor for taking a picture of the article surface to gain brightness informations for a plurality of two-dimensionally distributed pixels;

a fluctuation magnitude calculator means for calculating magnitudes of fluctuation in the brightness values along horizontal and vertical directions;

a fluctuation magnitude adder means for adding the fluctuation magnitudes on a pixel basis;

an averaging means for averaging the added fluctuation magnitudes on a pixel basis;

and a detector means for detecting presence of the defects when the mean fluctuation magnitude exceeds a predetermined value.

The fluctuation magnitude calculator means serves to gain the horizontal and vertical fluctuation magnitudes through the use of a first coefficient table emphasizing a horizontally extending contour and a second coefficient table emphasizing a vertically extending contour on the basis of N (m rows by n columns) brightness informations around a reference brightness information for one optional pixel.

Further, the averaging means is performed through the use of an averaging table of m rows by n columns on the basis of N (m rows by n columns) fluctuation magnitudes around a reference fluctuation magnitudes for one optional pixel.

In accordance with the apparatus described above, the fluctuation magnitude calculator means is adapted to gain magnitudes of horizontal and vertical fluctuation in brightness informations; the fluctuation magnitude adder means is adapted to average the added fluctuation magnitudes on a pixel basis; and the detector means is adapted to detect presence of the defects when the mean fluctuation magnitude exceeds a predetermined value. As a result, it becomes possible to precisely detect the miniature defects in the object article.

The fluctuation magnitude calculator means serves to gain the horizontal and vertical fluctuation magnitudes through the use of a first coefficient table emphasizing a horizontally extending contour and a second coefficient table emphasizing a vertically extending contour on the basis of N (m rows by n columns) brightness informations around a reference brightness information for one optional pixel.

In addition, the averaging means is performed through the use of an averaging table of m rows by n columns based on N (m rows by n columns) fluctuation magnitudes around a reference fluctuation magnitudes for one option pixel.

In accordance with the present invention, it becomes possible to precisely detect even the miniature defects in the object article by way of gaining magnitudes of fluctuation in the brightness informations for each of the pixels by user of an image sensor, gaining the horizontal and vertical fluctuation magnitudes through the use of a first coefficient table emphasizing a horizontally extending contour and a second coefficient table emphasizing a vertically extending contour on the basis of N (m rows by n columns) and vertical fluctuation magnitudes on a pixel basis; averaging the added fluctuation magnitudes, e.g., through the use of an averaging table of m rows by n columns on the basis of N (m rows by n columns) added fluctuation magnitudes; and detecting presence of the defects when the means fluctuation magnitude exceeds a predetermined value.

Another yet still further object of the present invention is to provide an apparatus for inspecting surface irregularity of object articles that makes it possible to detect not only low contrast specks out of an article surface but also miniature defects having a dimension of less than or slightly greater than the size of sensor pixel.

With the object is view, the invention provides an apparatus of inspecting surface irregularity of an object article having a surface of uniform or regular brightness, which comprises:

a brightness information generator for taking a picture of the article surface to gain brightness informations for a plurality of two-dimensionally distributed pixels;

a stain finder for examining presence of stains on the article surface on the basis of the brightness informations obtained by the brightness information generator to produce a first output;

a miniature defect finder for examining presence of miniature defects smaller in size than a unit pixel on the basis of the brightness informations obtained by the brightness information generator to produce a second output;

an output switching means for switching the first and second outputs into an appropriate electrical signals in a controlled manner; and a display for displaying the switched electrical signals in a viewable condition.

Specifically, the stain finder comprises: a brightness information adder for dividing the brightness informations for each of the pixels into a plurality of lattices each having a given number of row and column matrixes and then for adding the brightness informations of the pixels in the respective lattice to gain sum brightness values for each of the lattices; a fluctuation magnitude calculator for calculating magnitudes of fluctuation in the sum brightness values along horizontal and vertical directions with respect to said lattices; and a detector for detecting presence of the stains when the fluctuation magnitudes exceed a predetermined value.

Further, the brightness information adder comprises: a lattice divider for dividing the brightness informations for each of the pixels into a plurality of lattices each having a given number of row and column matrixes; a lattice position designator for designating positions of the lattices divided by the lattice divider; and an adder for adding the brightness informations on a lattice basis to gain sum brightness values for each of the lattices.

Furthermore, the fluctuation magnitude calculator comprises: a separator for separating horizontal and perpendicular brightness informations on the basis of of N (m rows by n columns) sum brightness values around a reference sum brightness value for one optional lattice; a horizontal fluctuation magnitude calculator for calculating horizontal fluctuation magnitude of the separated informations through the use of a first horizontal coefficient table; and a vertical fluctuation magnitude calculator for calculating vertical fluctuation magnitude of the separated brightness informations through the use of a second vertical coefficient table, preferably, each of the first and second tables is a Sobel filter.

In addition, the detector comprises: a threshold value generator for generating a signal indicative of threshold value; and a detection output feeder for proving a stain detection output signal when the horizontal and vertical fluctuation magnitudes exceed the threshold value.

More particularly, the detector comprises: a threshold value generator for generating a threshold value signal; a detection output feeder for providing a stain detection output signal when the horizontal and vertical fluctuation magnitudes exceed the threshold value; a labelling output feeder for providing an output signal indicative of area of the stain on the object article surface on the basis of the stain detection output signal from the detection output feeder; and a center position output feeder for providing an output signal indicative of a center position of the stain area on the basis of the stain detection output signal from the detection output feeder.

As an alternative, the detector comprises: a first threshold value generator for generating a signal indicative of a first threshold value with respect to the horizontal fluctuation magnitude; a second threshold value generator for generating a signal indicative of a second threshold value with respect to the vertical fluctuation magnitude; a first detection output feeder for providing a horizontal stain detection output signal when the horizontal fluctuation magnitude exceeds the first threshold value; and a second detection output feeder for providing a vertical stain detection output signal when the vertical fluctuation magnitude exceeds the second threshold value.

Specifically, the stain finder comprises: a brightness information adder for dividing the brightness informations for each of the pixels into a plurality of lattices each having a given number of row and column matrixes and then for adding the brightness informations of the pixels in the respective lattice to gain sum brightness values for each of the lattices; a fluctuation magnitude calculator for calculating magnitudes of fluctuation in the sum brightness values along horizontal and vertical directions with respect to said lattices; and a detector for detecting presence of the stains when the horizontal and vertical fluctuation magnitudes exceed a predetermined value;

wherein the brightness information adder comprises a lattice divider for dividing the brightness informations for each of the pixels into a plurality of lattices each having a given number of row and column matrixes, a lattice position designator for designating positions of the lattices divided by the lattice divider and an adder for adding the brightness informations on a lattice basis to gain sum brightness values for each of the lattices;

wherein the fluctuation magnitude calculator comprises a separator for separating horizontal and vertical brightness informations on the basis of N (m rows by n columns) sum brightness values around a reference sum brightness value for one optional lattice, a horizontal fluctuation magnitude calculator for calculating horizontal fluctuation magnitude of the separated informations through the use of a first horizontal coefficient table and a vertical fluctuation magnitude calculator for calculating vertical fluctuation magnitude of the separated brightness informations through the use of a second vertical coefficient table;

wherein the detector comprises a threshold value generator for generating a threshold value signal, a detection output feeder for providing a stain detection output signal when the horizontal and vertical fluctuation magnitudes exceed the threshold value, a labelling output feeder for providing an output signal indicative of area of the stain on the object article surface on the basis of the stain detection output signal from the detection output feeder and a center position output feeder for providing an output signal indicative of a center position of the stain area on the basis of the stain detection output signal from the detection output feeder; and wherein the switching means is designed to receive outputs of the separator, the horizontal fluctuation magnitude calculator and the vertical fluctuation magnitude calculator to produce switching signals of the outputs, and the display is adapted to display the switching signals fed from the output switching means.

The miniature defect finder comprises: a fluctuation magnitude calculator for gaining fluctuation magnitudes in the brightness informations along horizontal and vertical directions with respect to said lattices; a fluctuation magnitude adder for adding the horizontal and vertical fluctuation magnitudes for each of the pixels; a mean calculator for averaging the added fluctuation magnitudes for each of the pixels to provide mean fluctuation magnitudes; and a detector for detecting presence of the miniature defects when the mean fluctuation magnitudes exceed a predetermined value.

Further, the fluctuation magnitude calculator comprises: a horizontal differential calculator for gaining horizontal fluctuation magnitudes through the use of a first coefficient table emphasizing a horizontally extending contour on the basis of N (m rows by n columns) brightness informations around a reference brightness information for one optional pixel, and a vertical differential calculator for gaining vertical fluctuation magnitudes through the use of a second coefficient table emphasizing a vertically extending contour, based on the N brightness informations. Preferably, each of the first and the second coefficient tables is a Sobel filter.

The fluctuation magnitude adder comprises an adder for adding the horizontal and vertical fluctuation magnitudes on a pixel basis.

In addition, the mean calculator comprises an averaging filer for averaging the fluctuation magnitudes through the use of a table having m rows and n columns on the basis of N (m rows by n columns) fluctuation magnitudes around a reference fluctuation magnitude for one optional pixel.

Further, the detector comprises a threshold value generator for generating a threshold value signal and a detection output feeder for providing a defect detection output signal when the mean fluctuation magnitudes exceed the threshold value.

Furthermore, the miniature defect finder comprises a fluctuation magnitude calculator for gaining fluctuation magnitudes in the brightness informations along horizontal and vertical directions, a fluctuation magnitude adder for adding the horizontal and vertical fluctuation magnitudes for each of the pixels, a mean calculator for averaging the added fluctuation magnitudes for each of the pixels to provide mean fluctuation magnitudes and a detector for detecting presence of the miniature defects when the mean fluctuation magnitudes exceed a predetermined value;

wherein the fluctuation magnitude calculator comprises a horizontal differential calculator for gaining horizontal fluctuation magnitudes through the use of a first coefficient table emphasizing a horizontally extending contour on the basis of N (M rows by n columns) brightness informations around a reference brightness information for one optional pixel, and a vertical differential calculator for gaining vertical fluctuation magnitudes through the use of a second coefficient table emphasizing a vertically extending contour, based on the N brightness informations;

wherein the fluctuation magnitude adder comprises an adder for adding the horizontal and vertical fluctuation magnitudes on a pixel basis;

wherein the mean calculator comprises an averaging filter for providing mean fluctuation magnitudes through the use of a table having m rows and n columns on the basis of N (m rows by n columns) fluctuation magnitudes around a reference fluctuation magnitude for one optional pixel;

wherein the detector comprises a threshold value generator for generator for generating a threshold value signal and a detection output feeder for providing an detection output signal when the mean fluctuation magnitudes exceed a reference value; and wherein the output switching means is designed to receive outputs of the horizontal differential calculator, the perpendicular differential calculator, the adder, the averaging filter and the detection output feeder to provide switching signals of the outputs, and the display is adapted to display the switching signals fed from the detection output feeder.

Still furthermore, the stain finder comprises a brightness information adder for dividing the brightness informations for each of the pixels into a plurality of lattices each having a given number of row and column matrixes and then for adding the brightness informations of the pixels in the respective lattice to gain sum brightness values for each of the lattices, a fluctuation magnitude calculator for calculating magnitudes of fluctuation in the sum brightness values along horizontal and vertical directions and a detector for detecting presence of the stains when the horizontal and vertical fluctuation magnitudes exceed a predetermined value;

wherein the brightness information adder comprises a lattice divider for dividing the brightness informations for each of the pixels into a plurality of lattices each having a given number of row and column matrixes, a lattice position designator for designating positions of the lattices divided by the lattice divider and an adder for adding the brightness informations of the pixels in the respective lattice to gain sum brightness values for each of the lattices;

wherein the fluctuation magnitudes calculator comprises a separator for separating horizontal and vertical brightness information on the basis of N (m rows by n columns) sum brightness values around a reference sum brightness value for one optional pixel, a horizontal fluctuation magnitude calculator for calculating horizontal fluctuation magnitude of the separated brightness informations through the use of a first horizontal coefficient table and a vertical fluctuation magnitude calculator for calculating vertical fluctuation magnitude of the separated brightness informations through the use of a second vertical coefficient table;

wherein the detector comprises a threshold value generator for generating a threshold value signal and a detection output feeder for providing a stain detection output signal when the horizontal and perpendicular fluctuation magnitudes exceed the threshold value;

wherein the miniature defect finder comprises a fluctuation magnitude calculator for gaining fluctuation magnitudes in the brightness informations along horizontal and vertical directions, a fluctuation magnitude adder for adding the horizontal and vertical fluctuation magnitudes for each of the pixels, a mean calculator for averaging the added fluctuation magnitudes for each of the pixels to provide mean fluctuation magnitudes and a detector for detecting presence of the miniature defects when the mean fluctuation magnitudes exceed a predetermined value;

wherein the fluctuation magnitude calculator comprises a horizontal differential calculator for gaining horizontal fluctuation magnitudes through the use of a first coefficient table emphasizing a horizontally extending contour on the basis on N (m rows by n columns) brightness informations around a reference brightness information for one optional pixel, and a vertical differential calculator for gaining vertical fluctuation magnitudes through the use of a second coefficient table emphasizing a vertically extending contour, based on the N brightness informations;

wherein the fluctuation magnitude adder comprises an adder for adding the horizontal and vertical fluctuation magnitudes on a pixel basis;

wherein the mean calculator comprises an averaging filter for providing mean fluctuation magnitudes through the use of a table having m rows and n columns on the basis of N (m rows by n columns) fluctuation magnitudes around a reference fluctuation magnitude for one optional pixel;

wherein the detector comprises a threshold value generator for generating a threshold value signal and a detection output feeder for providing an detection exceed a predetermined value; and wherein the output switching means is designed to receive outputs of the separator, the horizontal fluctuation magnitude calculator, the vertical fluctuation magnitude calculator, the horizontal differential calculator, the vertical differential calculator, the adder, the averaging fitter and the detector to provide switching signals of the outputs, and the display is adapted to display the switching signals fed from the output switching means.

BRIEF DESCRIPTION OF THE DRAWINGS

Other object and features of the invention will become apparent from the following detailed description of the preferred embodiment taken in conjunction with the accompanying drawings in which:

FIG. 2 illustrates a succession of pixels obtained by a line sensor of the prior art apparatus and a technique of calculation brightness informations to detect stains;

FIGS. 3(a) and 3(b) are graphical representations showing the brightness relative to the pixel position;

FIG. 17 is an exemplary view showing the horizontal Sobel filter;

FIG. 18 is an exemplary view showing the vertical Sobel filter;

DETAILED DESCRIPTION OF THE PREFERRED EMBODIMENT

Figure 1:
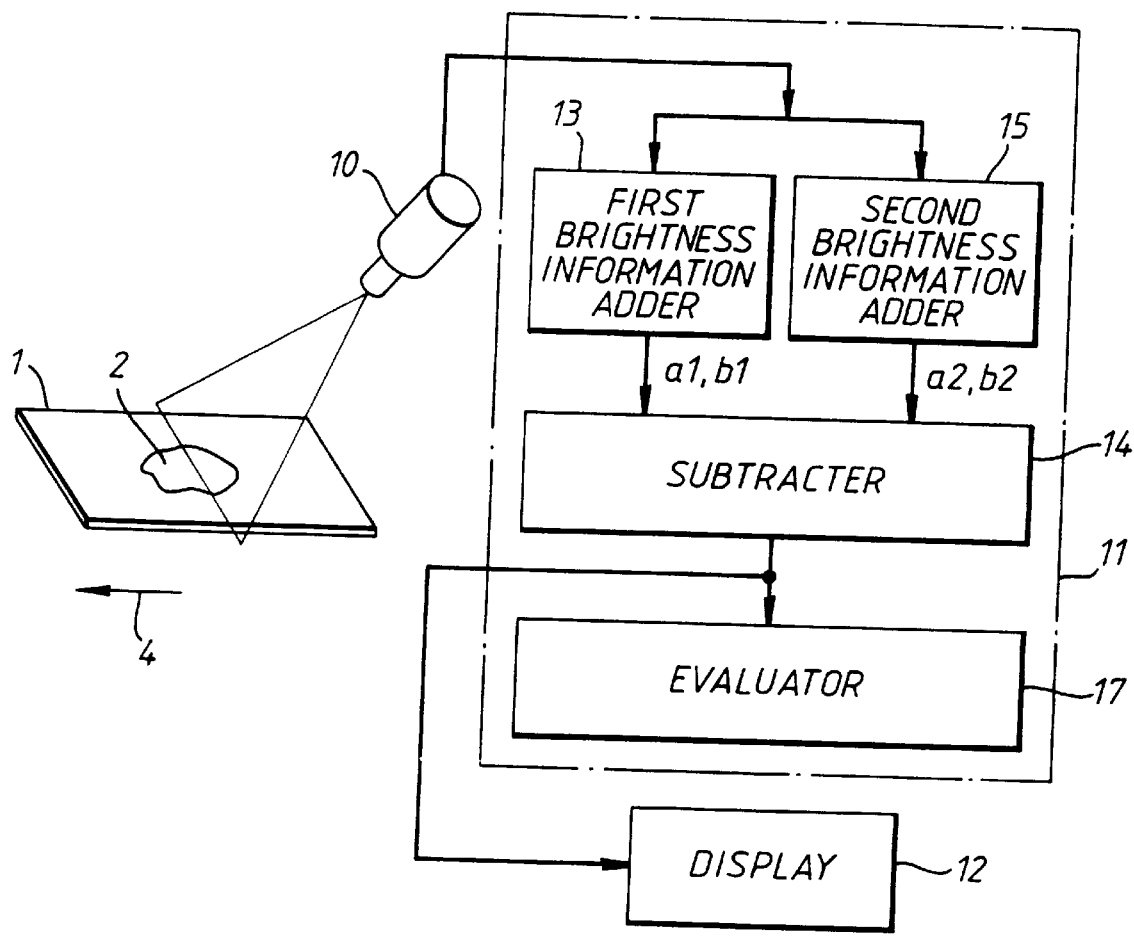
FIG. 1 is a block diagram showing a prior art apparatus of inspecting surface irregularity present on an object article.
Figure 4:
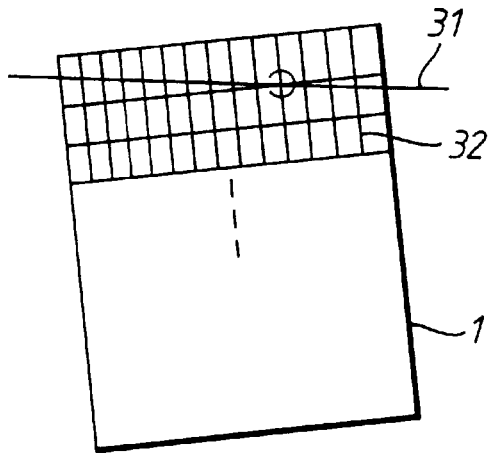
FIG. 4 illustrates an object article having a lattice-like pattern whose horizontal line is out of alignment with the detection line of the line sensor.
Figure 5:
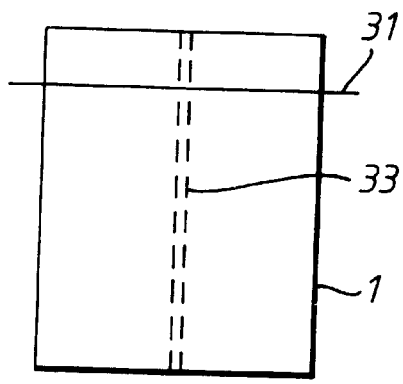
FIG. 5 illustrates a perpendicularly extending stain on the object article which is orthogonal to the detection line of the line sensor.
Figure 6:
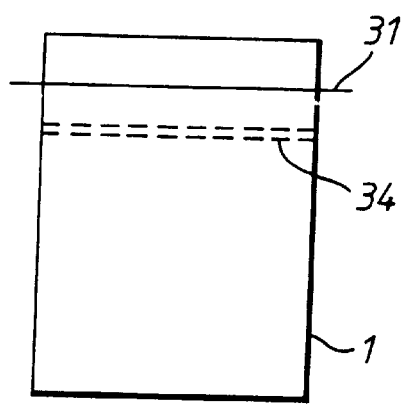
FIG. 6 shows a horizontally extending stain on the object article which is parallel to the detection line of line sensor.
Figure 7:
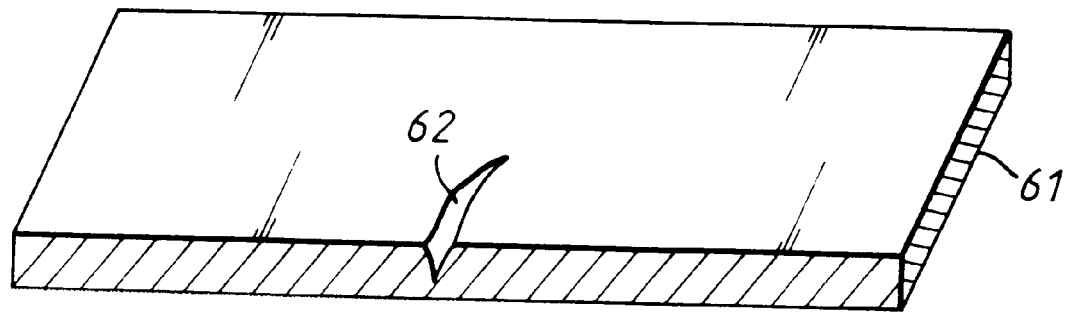
FIG. 7 is a partially cutaway perspective view depicting a defect or flaw appearing on an aluminium sheet.
Figure 8:
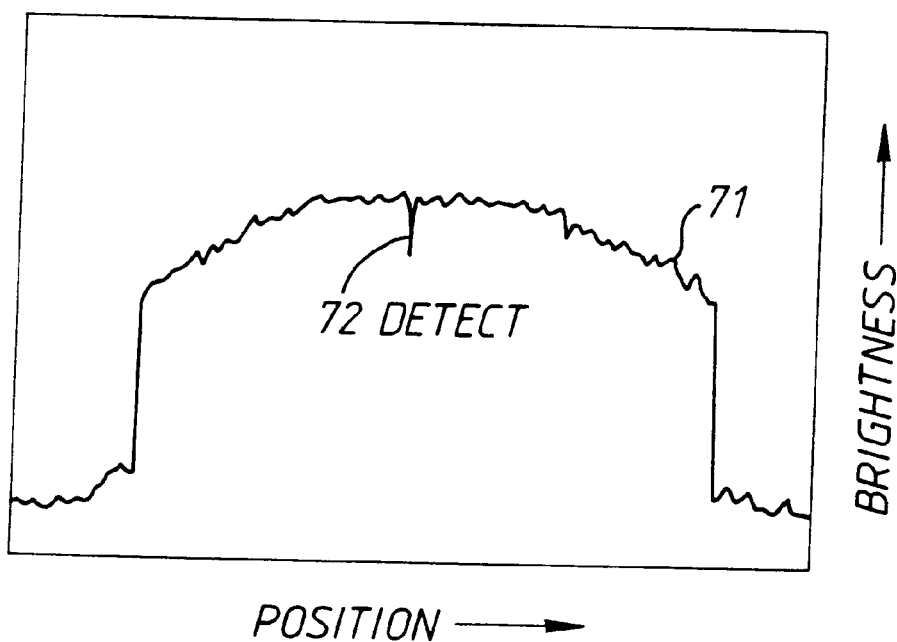
FIG. 8 illustrates graphically brightness informations of a pixel which intersects a centrally located miniature defect, the brightness informations involving a shading and/or high frequency noise.
Figure 9:
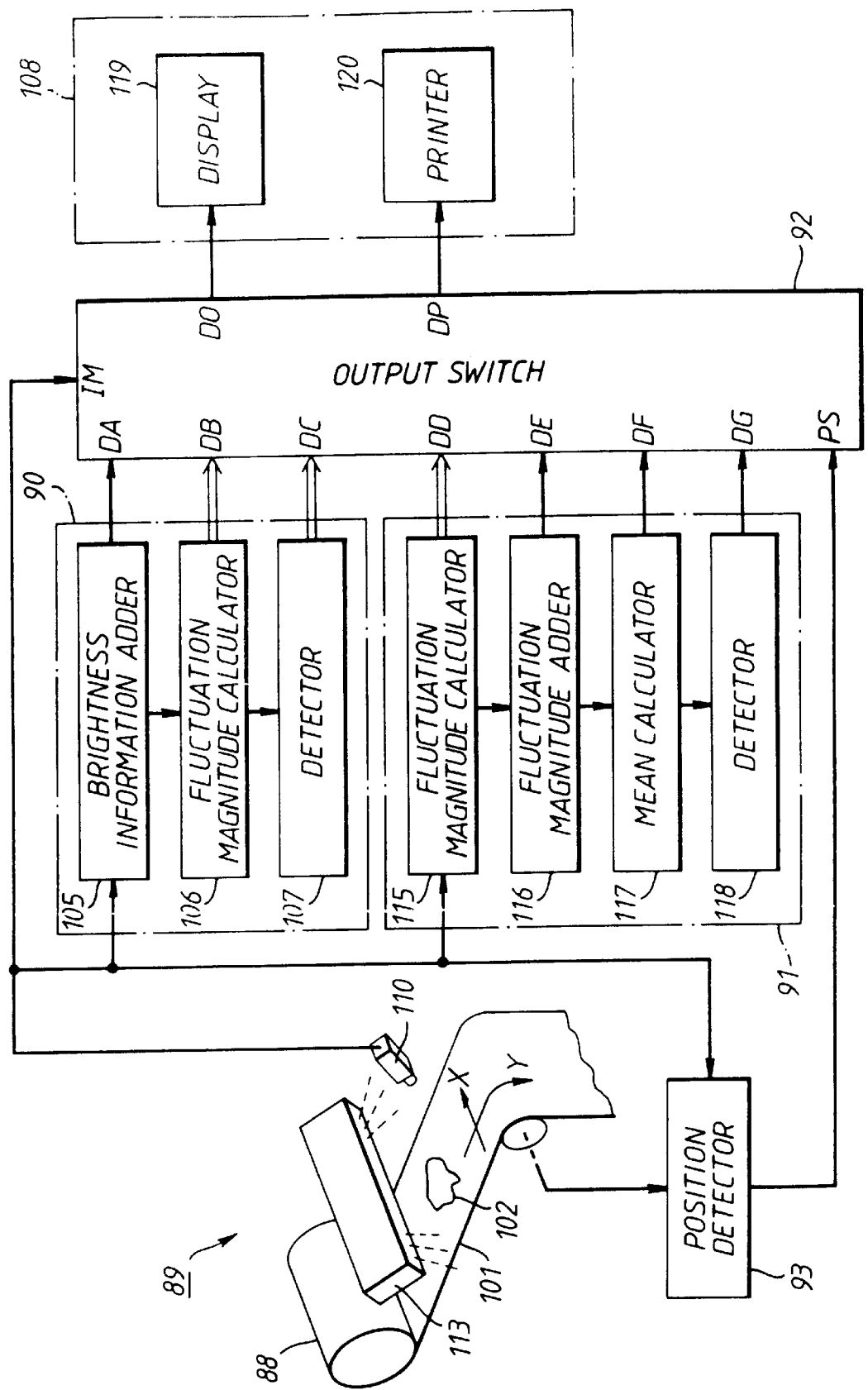
FIG. 9 is a block diagram showing a surface irregularity inspection apparatus in accordance with the present invention.

Referring now to FIG. 9, there is shown a surface irregularity inspection apparatus in accordance with an embodiment of the present invention, which is particularly suitable for detecting presence of a stain 102 or miniature defect possibly appearing on an object article, e.g., steel plate 101, by use of a suitable sensor. The inspection apparatus serves to detect the stain 102 or defect present on the surface of the steel plate 101 as it is transferred toward a machining station from a roll 88. In the illustrated embodiment, the inspection apparatus comprises an input feeder 89, a stain finder 90, a defect finder 91, output switch 92 and a display 108, each operatively coupled to one another.

Figure 10:
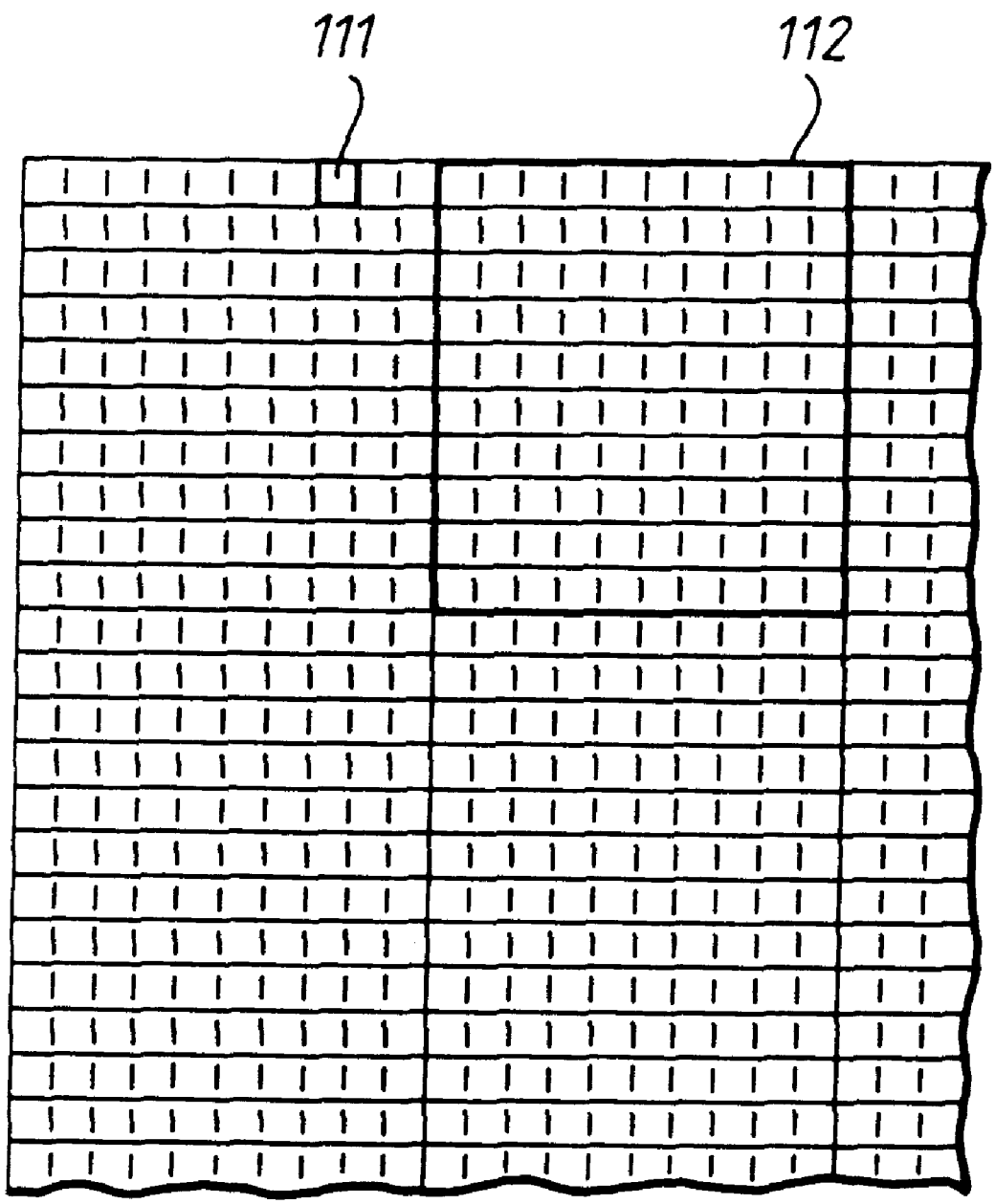
FIG. 10 depicts that the brightness informations for each of the pixels is divided into a lattice having a plurality of row and column matrixes.

The input feeder 89 includes a line sensor 110 having a CCD camera among other things, a lighting device 113 for lighting an object article to ensure efficient image-taking by the line sensor 110 and a position detector 93 for determining which position of the steel plate 101 is presently image-taken by the line sensor 110. The line sensor 110 is adapted to take a picture of the object article to obtain brightness informations for each of the pixels 111 which are two-dimensionally distributed as shown in FIG. 10. The lighting device 113 is designed to illuminate the object article 101 by use of a reflected light. Depending on the type of object articles to be inspected, it may be possible to use a transmitted light.

The stain finder 90 includes a brightness information adder 105 receiving image signals IM from the line sensor 110, a fluctuation magnitude calculator 106 and a detector 107. On the other hand, the defect finder 91 is provided with a fluctuation magnitude calculator 115, a fluctuation magnitude adder 116, a means calculator 117 and a detector 118. The output switch 92 serves to selectively couple the various outputs of the stain finder 90 and the defect finder 91 to the display 108 in a controlled manner.

The display 108 consists essentially of a cathode ray tube 119 for displaying surface conditions of the object article on a real time basis and a printer 120 for printing data on the position and size of detected stain or defect. In other words, the display 108 is operable to display horizontal and vertical fluctuation magnitudes obtained in the fluctuation magnitude calculator 106. Another role of the display 108 is to show brightness informations for the respective pixel gained by the line sensor 110 and sum brightness values for each of the pixels produced in the brightness information adder 105. It is also possible to display output conditions of the fluctuation magnitude calculator 106 and the detector 107.

Figure 11:
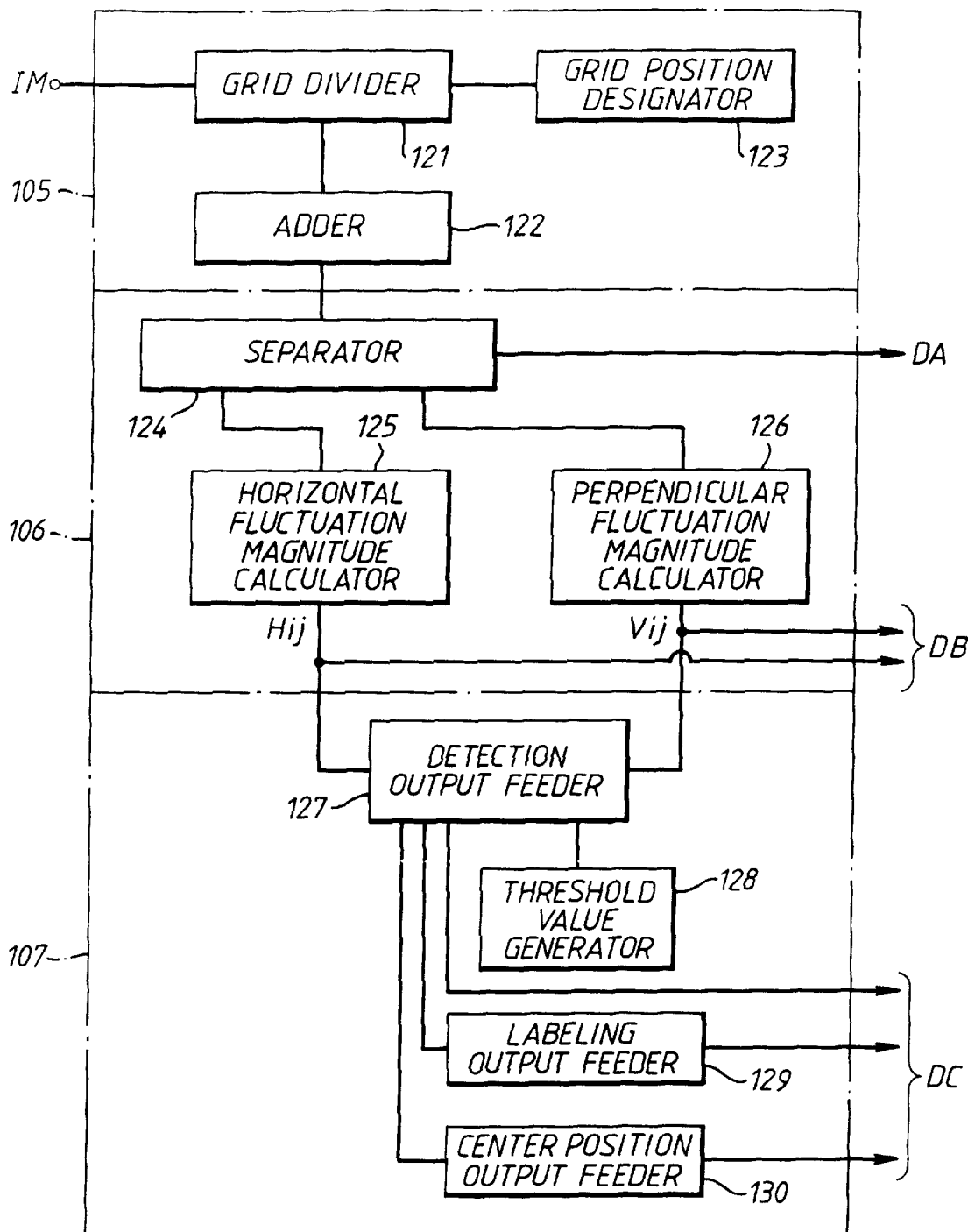
FIG. 11 is a block diagram showing a stain finder that constitutes the surface irregularity inspection apparatus in accordance with the present invention.

FIG. 11 show construction of the stain finder 90 in more detail. The brightness information adder 105 includes a lattice divider 121 for dividing the brightness informations obtained by the line sensor 110 for each of the pixels into a plurality of lattices 112 each having a given number of row and column matrixes, an adder 122 for adding the brightness informations for the respective pixel contained within each of the lattices to gain sum brightness values for each of the lattices and a lattice position designator 123 for designating site, scan area and scan position of the lattices.

The fluctuation magnitude calculator 106 includes a separator 124 for separating horizontal and vertical values from the sum brightness values fed by the brightness information adder, a horizontal fluctuation magnitude calculator 125 for gaining horizontal fluctuation magnitudes of the sum brightness values for the respective lattice by use of a 3 row and 3 column matrix and a vertical fluctuation magnitude calculator 126 for gaining vertical fluctuation magnitudes of the sum brightness values for the respective lattice by use of the 3 row and 3 column matrix.

The detector 107 includes a detection output feeder 127 for providing a stain detection output signal DC by way of adding the horizontal and perpendicular fluctuation magnitudes, a threshold value generator 128 for selecting a predetermined threshold value, a labelling output feeder 129 for providing an output signal indicative of area of the stain on the basis of the stain detection output signal DC fed from the detection output feeder 127 and a center position output feeder 130 for providing an output signals indicative of center position coordinates of the stain area. The detector 107 of the construction stated above can detect the stain present on the object article by use of the horizontal and vertical fluctuation magnitudes attained in the fluctuation magnitude calculator 106.

Figure 12:
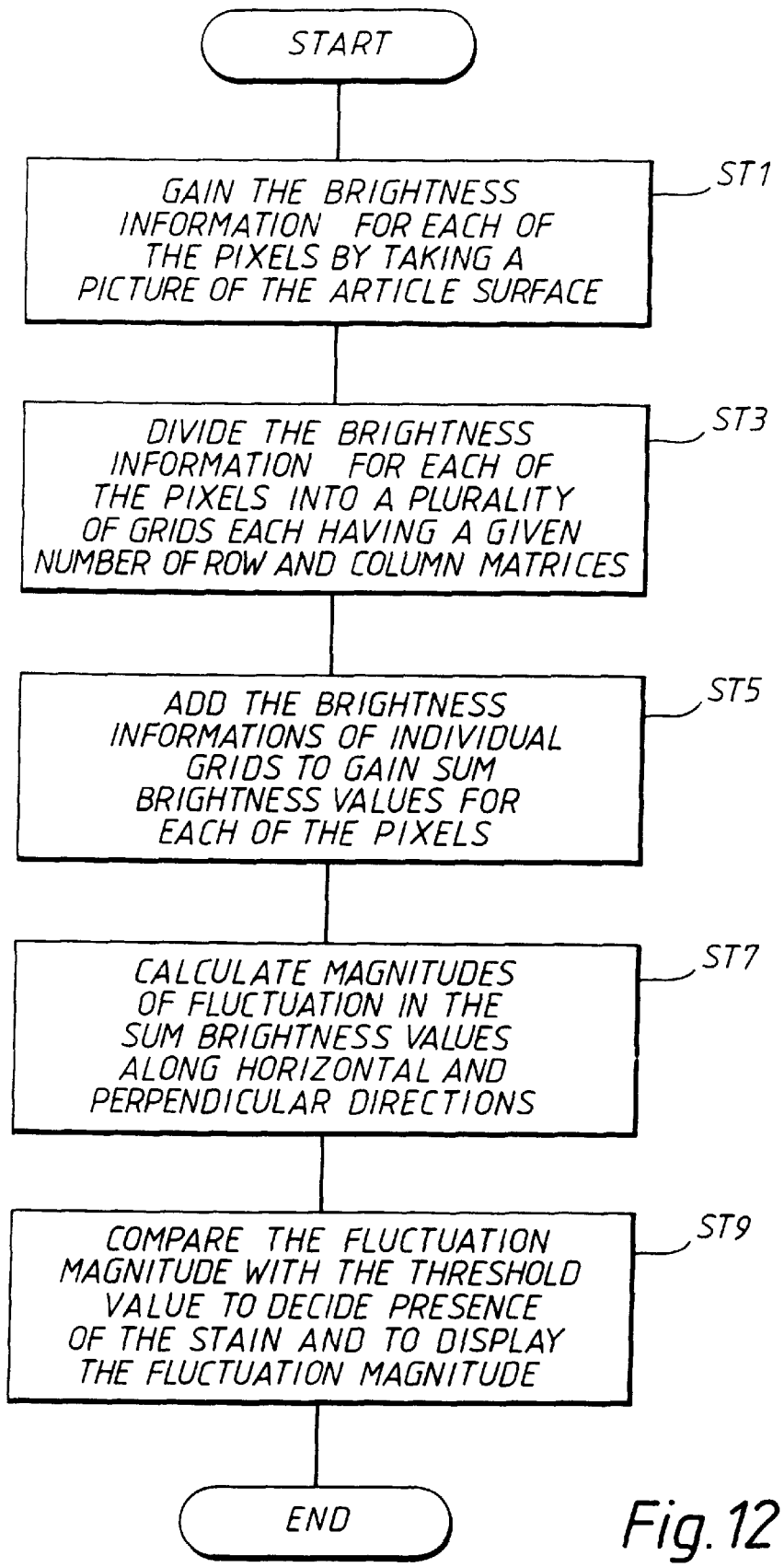
FIG. 12 is a flow chart showing operation of the stain finder as depicted in FIG. 11.
Figure 13:
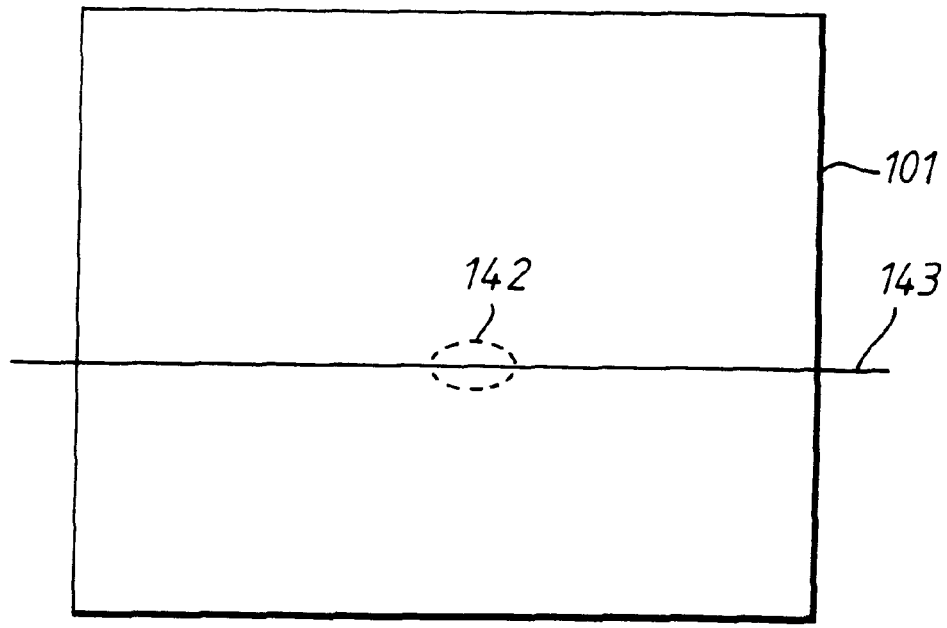
FIG. 13 shows an exemplary pictorial information of the object article having a centrally located stain.

With reference to FIG. 12, operation of the above-mentioned surface irregularity inspection apparatus will now be described hereinbelow. It is assumed that the object article 101 has an elliptical stain 142 at its center, as illustrated in FIG. 13, and further that the line sensor 110 scans the object article along the transverse line 143.

Figure 14:
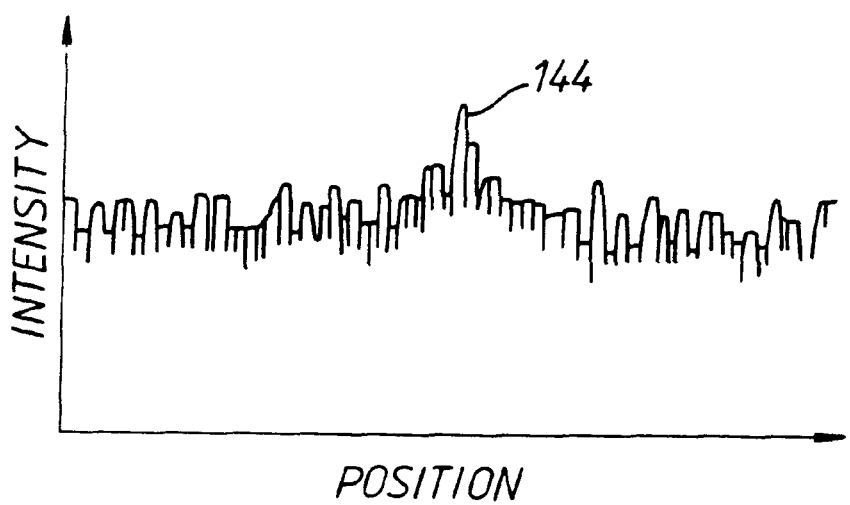
FIG. 14 is a view graphically showing the brightness informations obtained along the transverse line of FIG. 13.

At the outset, the object article is photographed by the line sensor 110 to gain brightness information for each of the pixels, with individual brightness information subdivided into 256 levels of intensity ranging from 0 to 255 (Step 1). The brightness informations for the pixels lying along the transverse line 143 of FIG. 13 may be displayed by a curve 144 on the display 108, as illustrated in FIG. 14.

Figure 15:
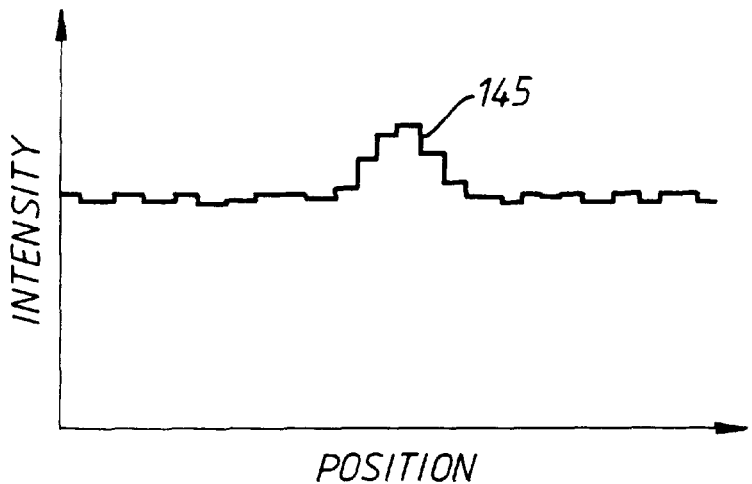
FIG. 15 is a view graphically representing the sum brightness values for a lattice corresponding to the transverse line of FIG. 13, in which each group of the sun brightness values are normalized with the greatest values.

Once the brightness informations are obtained for each of the pixels, the fluctuation magnitude calculator 106 first divides the brightness informations into a plurality of lattices 112 as shown in FIG. 10 and then adds the brightness informations of the pixels contained in the respective lattice to gain sum brightness values for each of the lattices. While each of the lattices consists of 10 row and 10 columns to contain 10 by 10 pixels therein, the number of pixels contained in one lattice is not limited thereto and may be changed in practical use. The curve 145 of FIG. 15 is obtained by way of normalizing the sum brightness values of the lattice 112 shown in FIG. 13, with its greatest value.

The fluctuation magnitude calculator to calculates horizontal fluctuation magnitude $H_{ij}$ and vertical fluctuation magnitude $V_{ij}$ in the sum brightness values of each of the lattices, on the basis of a 3 row and 3 column matrix (Step 3). The "horizontal" and "vertical" directions are aligned with respect to said lattices.

Figure 16:
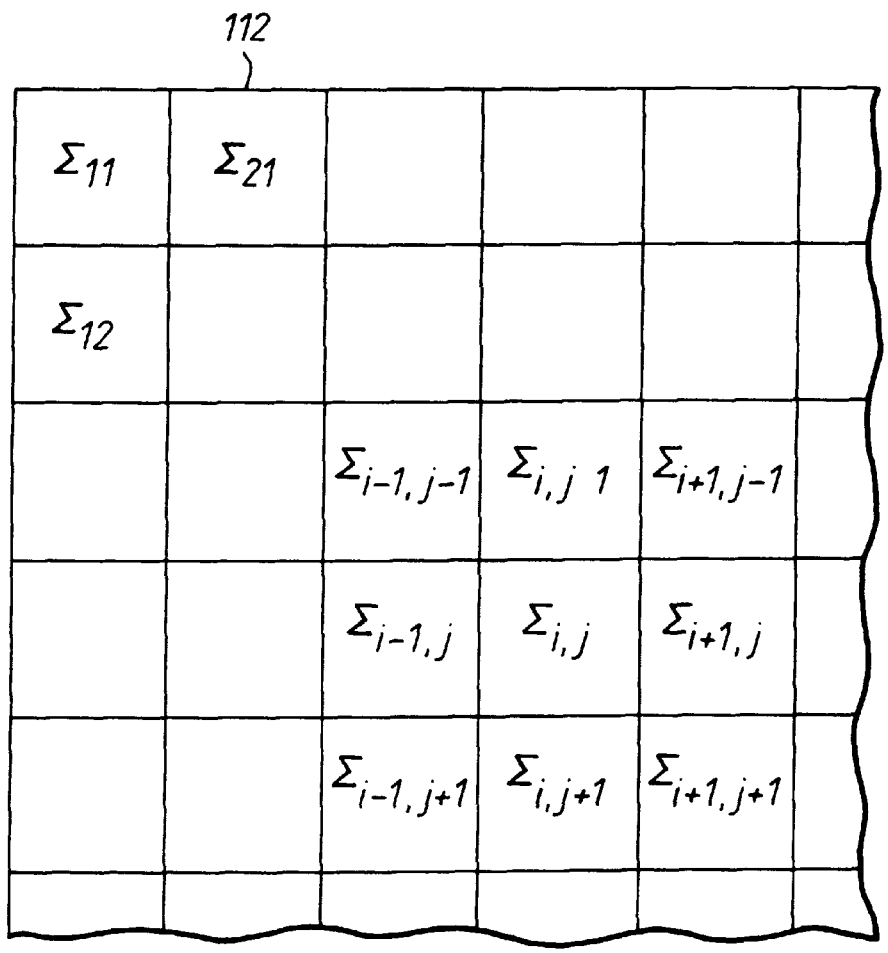
FIG. 16 shows how to gain horizontal and vertical fluctuation magnitudes of the sum brightness values for an optional pixel.
Figures 17, 18:
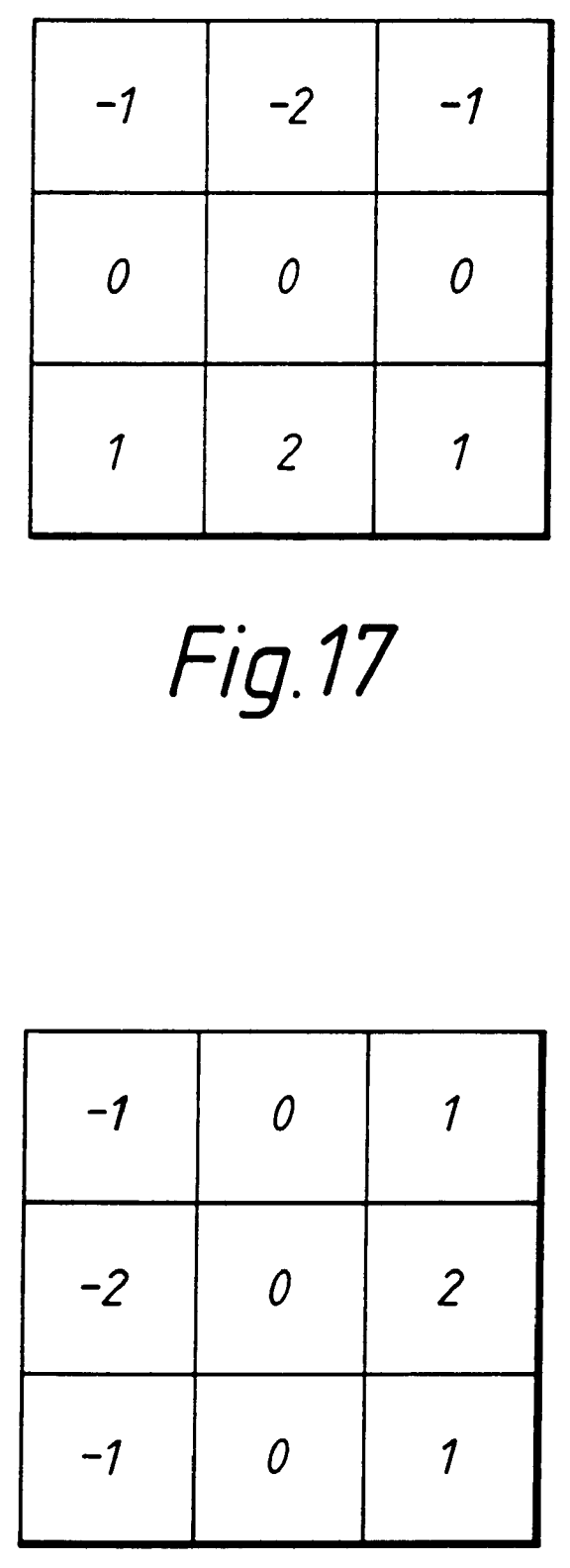

As an example, the horizontal fluctuation magnitude $H_{ij}$ and the vertical fluctuation magnitude $V_{ij}$ for the sum brightness value $\Sigma_{ij}$ of one optional lattice can be calculated through the use of a horizontal Sobel filter (first coefficient table) shown in FIG. 16 and a vertical Sobel filter (second coefficient table) shown in FIG. 17, based on 9 (3 rows by 3 columns) sum brightness values around the sum brightness value $\Sigma_{ij}$. The following equations may be used in calculating the fluctuation magnitudes Hij and Vij:

$$H_{ij} = \left| -\sum_{i-1,j-1} -2\sum_{i,j-1} -\sum_{i+1,j-1} +\sum_{i-1,j+1} +2\sum_{i,j+1} +\sum_{i-1,j+1} \right| \quad [1]$$

$$V_{ij} = \left| -\sum_{i-1,j-1} +\sum_{i+1,j-1} -2\sum_{i-1,j} +2\sum_{i+1,j} -\sum_{i-1,j+1} +\sum_{i+1,j+1} \right| \quad [2]$$

Once the horizontal and vertical fluctuation magnitudes $H_{ij}$ and $V_{ij}$ are found, the fluctuation magnitude calculator 106 adds those fluctuation magnitude $H_{ij}$ and $V_{ij}$ to gain total fluctuation magnitude $C_{ij}$ for each of the lattices (Step 7).

The total fluctuation magnitude $C_{ij}$ cannot be gained with respect to the respective outermost lattice, inasmuch as there exist no nine lattices around any of the outermost lattices. Nevertheless, it is still possible to detect presence of the stain on the outermost lattices, because the sum brightness value thereof shall be necessarily used in the course of calculating the total fluctuation magnitudes $C_{ij}$ of the immediately inner lattices. Although the total fluctuation magnitudes $C_{ij}$ is gained through the use of a Sobel filter, it would be possible to use other suitable coefficient filters or matrixes of e.g., 2 rows/2 columns or 3 rows/1 column.

Figure 19:
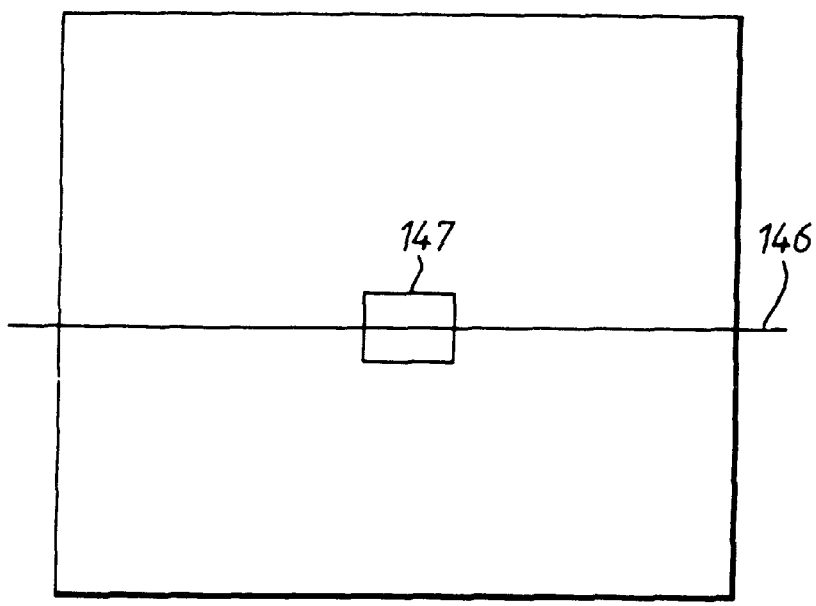
FIG. 19 illustrates the fluctuation magnitudes for each of the lattices in a normalized form.
Figure 20:
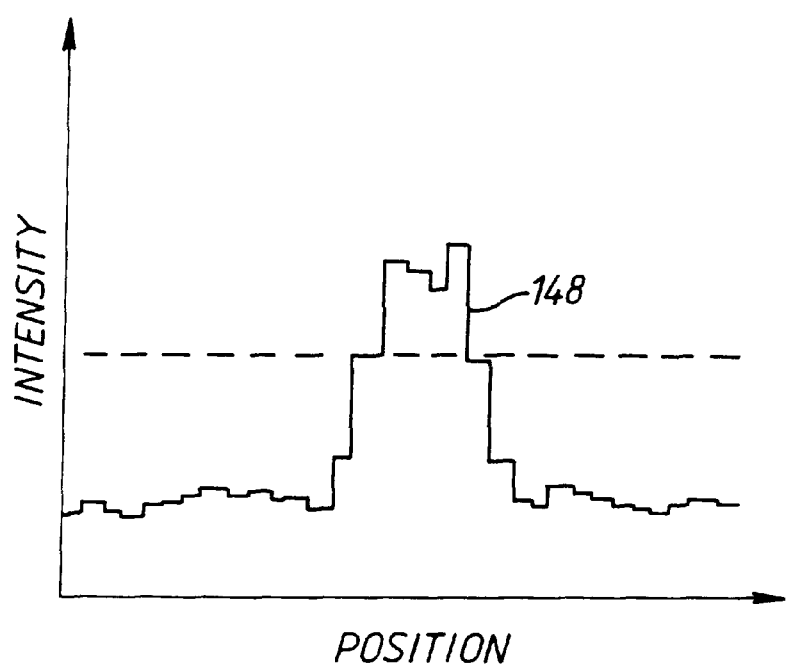
FIG. 20 is a view graphically illustrating the normalized fluctuation magnitudes of the lattice which corresponds to the transverse line of FIG. 19.

The detector 107 compares the total fluctuation magnitudes $C_{ij}$ with a predetermined threshold value and decides the stain to exist if the fluctuation magnitude $C_{ij}$ is greater than the threshold value (Step 9). On the other hand, the display 108 serves to normalize the total fluctuation magnitudes Cij by use of equation [3] and then displays the result as shown in FIG. 19.

$$S_{ij} = C_{ij} \times 255 / C_{max} \quad [3]$$

wherein $S_{ij}$ is the normalized fluctuation magnitude and Cmax is the greatest total fluctuation magnitude. The curve 148 shown in FIG. 20 graphically represents the normalized fluctuation magnitude $S_{ij}$ for the lattice 147 corresponding to the transverse line 148 of FIG. 19. It can be seen in FIG. 20 that the stain 142 of FIG. 13 is emphasized remarkably.

As set forth above, the brightness informations obtained by the line sensor 110 are divided into a plurality of lattices having row and column pixel matrixes. The brightness informations for the pixels in each of the lattices are then added to provide sum brightness values of the individual lattice, thereby emphasizing the stain. A further emphasis is placed on the stain by virtue of gaining, within a 3 row and 3 column matrix, the horizontal fluctuation magnitude $H_{ij}$ and the vertical fluctuation magnitude $V_{ij}$ of the sum brightness values on a lattice basis. Subsequently, the total fluctuation magnitude $C_{ij}$ is compared with a predetermined threshold value to decide existence of the stain in case where the fluctuation magnitude $C_{ij}$ is greater than the threshold value.

As a result, since the stain is significantly emphasized by way of gaining the horizontal and vertical fluctuation magnitudes $H_{ij}$ and $V_{ij}$, it becomes possible to detect the stain with no or little dependency on the scanning direction of the object article. As for the object article having a lattice-like pattern on its surface, e.g., LCD color filter, the stain detection can be carried out with a high accuracy, regardless of the skew angle of the object article with respect to the detection line.

As an alternative, it would be possible to decide the existence of the stain by use of the horizontal and vertical fluctuation magnitudes $H_{ij}$ and $V_{ij}$ themselves, without having to use the total fluctuation magnitudes $C_{ij}$ at all.

Figure 21:
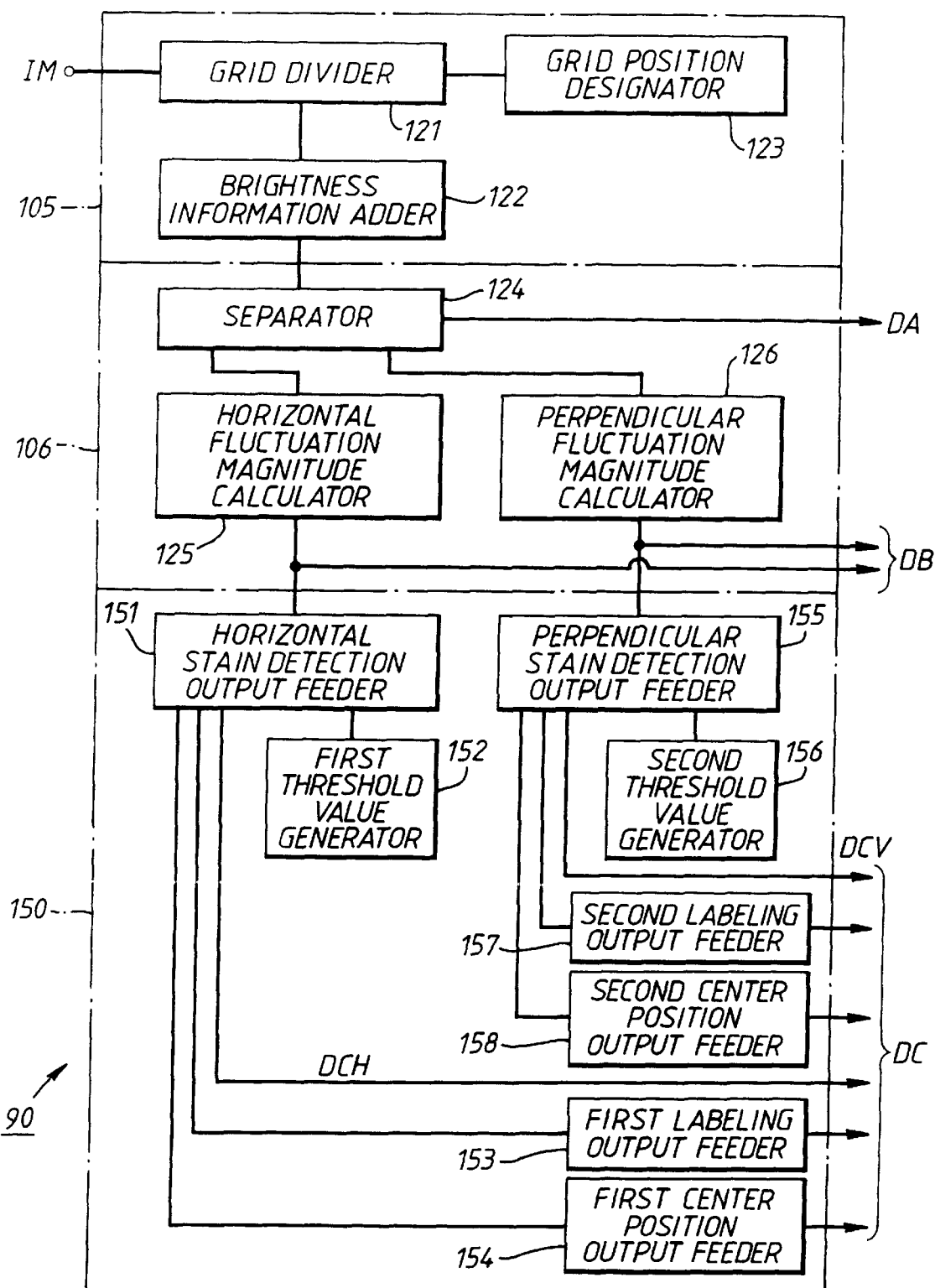
FIG. 21 is a block diagram showing another embodiment of the surface irregularity inspection apparatus.

Specifically, the detector 150, as shown in FIG. 21, may comprise a horizontal stain detection output feeder 151 for providing a horizontal stain detection output DCH, a first threshold value generator 152 for selecting a first predetermined threshold value, a first labelling output feeder 153 for providing an output indicative of area of the stain on the basis of the horizontal stain detection output DCH, a first center position output feeder 154 for providing an output indicative of center position coordinates of the stain area, a vertical stain detection output feeder 155 for providing a vertical stain detection output DCV, a second threshold value generator 156 for selecting a second predetermined threshold value, a second labelling output feeder 157 for providing an output indicative of area of the stain on the basis of the horizontal stain detection output DCV and a second center position output feeder 158 for providing an output indicative of center position coordinates of the stain area. The detector 150 of the above construction makes it possible to detect the stain present on the object article by using each of the horizontal and perpendicular fluctuation magnitudes which are separately fed from the fluctuation magnitude calculator 106.

Although the present embodiment is directed to detecting a stain located at the center of a steel plate, it would also be possible to detect those stains that exist on a LCD color filter, a TV shadow mask, a variety of films and other sheet materials.

Figure 22:
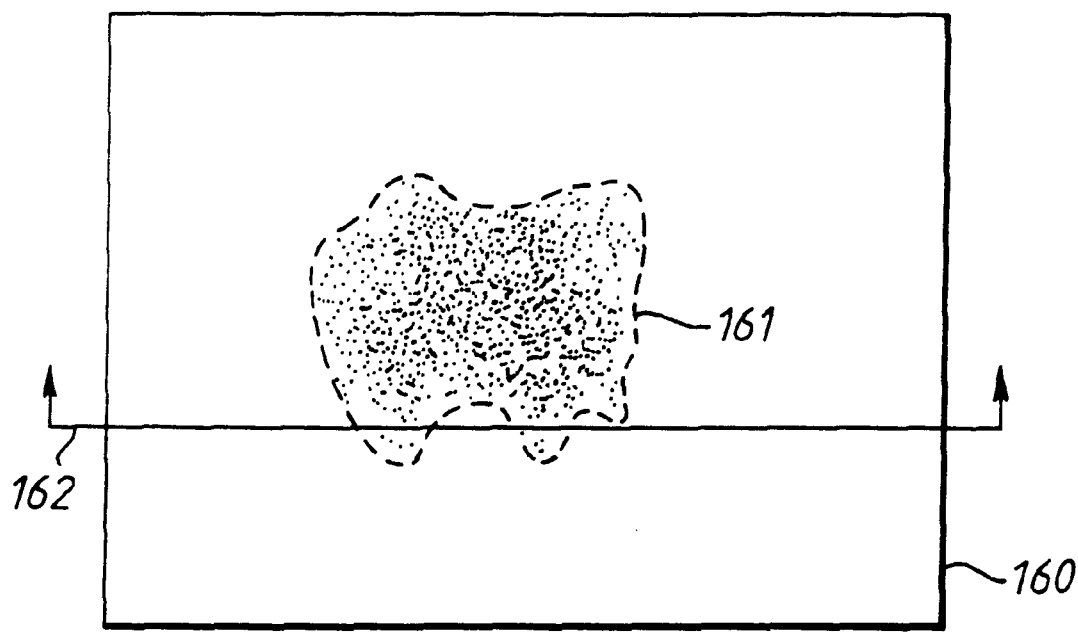
FIG. 22 shows another pictorial information of the object article having a centrally located stain.
Figure 23:
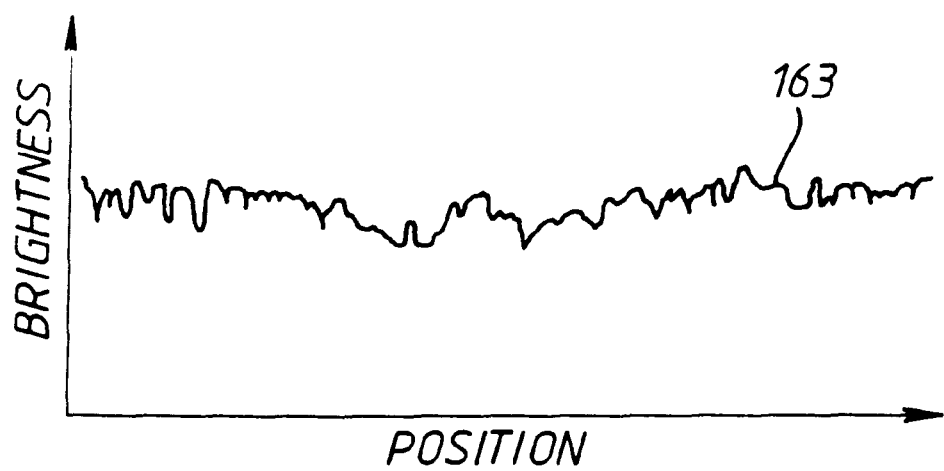
FIG. 23 is a view graphically representing the brightness informations obtained along the transverse line of FIG. 22.
Figure 24:
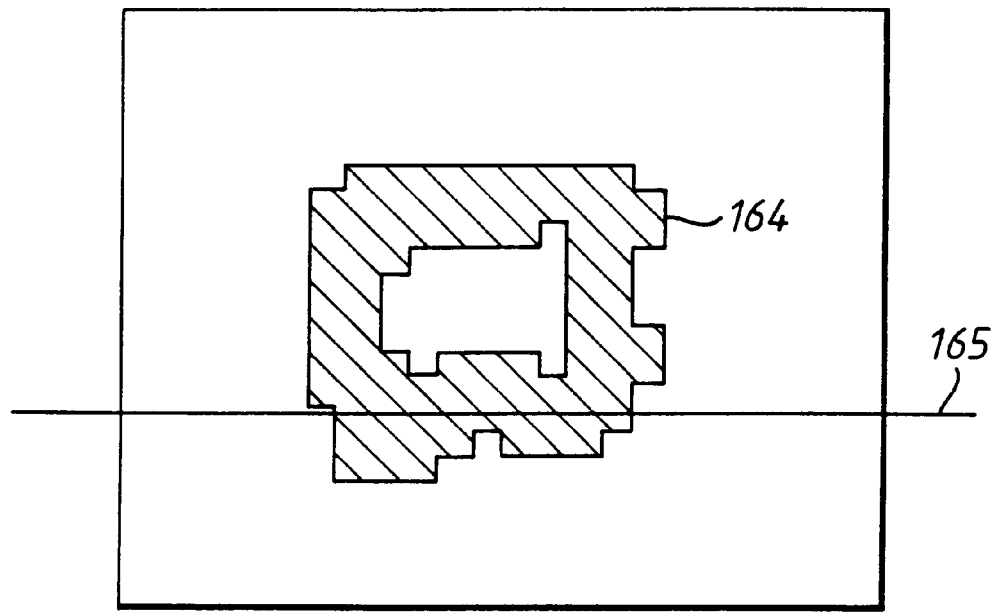
FIG. 24 is a view representing the sum brightness values for a lattice corresponding to the transverse line of FIG. 22, in which each group of the sum brightness values are normalized with the greatest values.
Figure 25:
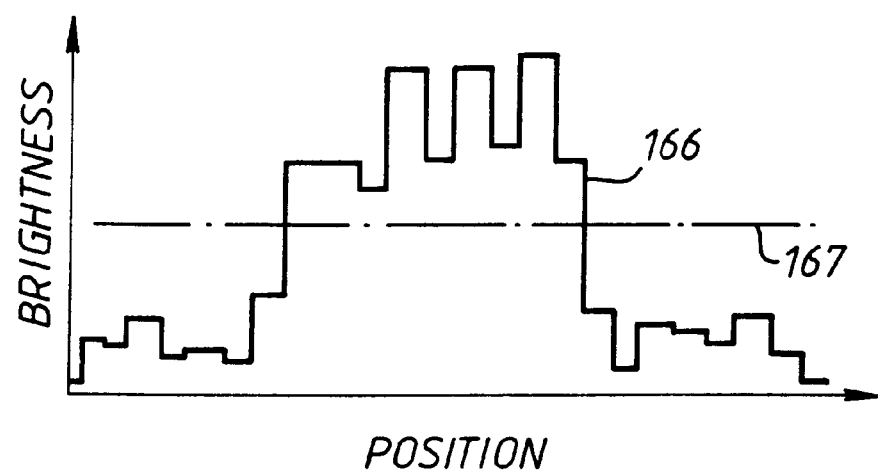
FIG. 25 is a graphical representation illustrating the normalized fluctuation magnitudes for the lattice which corresponds to the transverse line of FIG. 24.

For instance, the novel method and apparatus of inspecting surface irregularity is able to positively detect even an unclear speck area 161 appearing on a moisture-containing drug carrier 160 of nonwoven fabric, as illustrated in FIG. 22. The curve 163 of FIG. 23 shows the brightness informations obtained by the line sensor 110 along the transverse line 162 of FIG. 22. The brightness informations may be processed in the stain finder 90 and then displayed by the display 100, as indicated in FIG. 24 which shows the speck area as a hatched zone 164. The curve 166 of FIG. 25 indicates the brightness informations obtained along the transverse line 165 of FIG. 24. In FIG. 25, the transversely extending dotted line 167 represents the threshold value defining a lower limit of the hatched zone 164.

Figure 26:
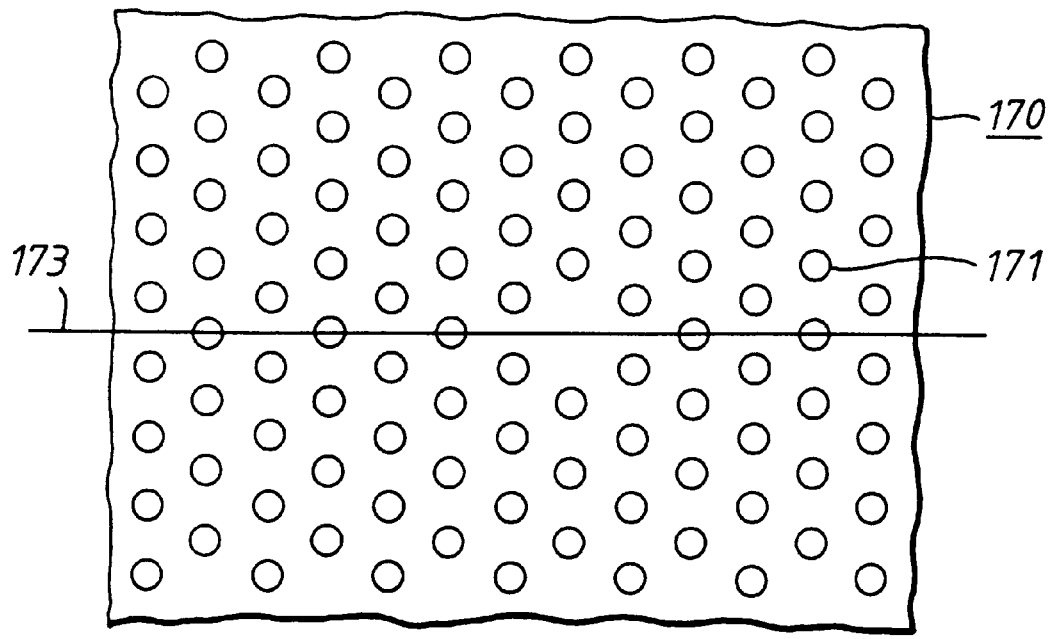
FIG. 26 is a top view of the shadow mask having a defect at it center.

Additionally, the surface irregularity inspection apparatus stated above has the capability to find a defect of penetration holes 171 formed through the CRT shadow mask 170 as shown in FIG. 26.

Figure 27:
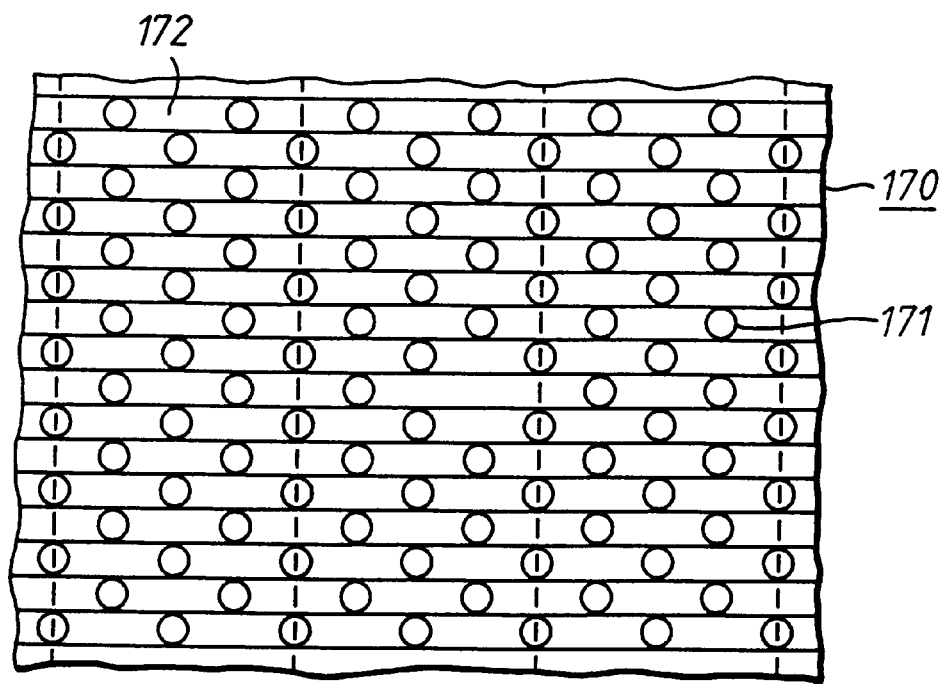
FIG. 27 shows that the brightness informations for each of the pixels obtained from the picture of the shadow mask are divided into a plurality of lattices consisting of row and column matrixes.
Figure 28:
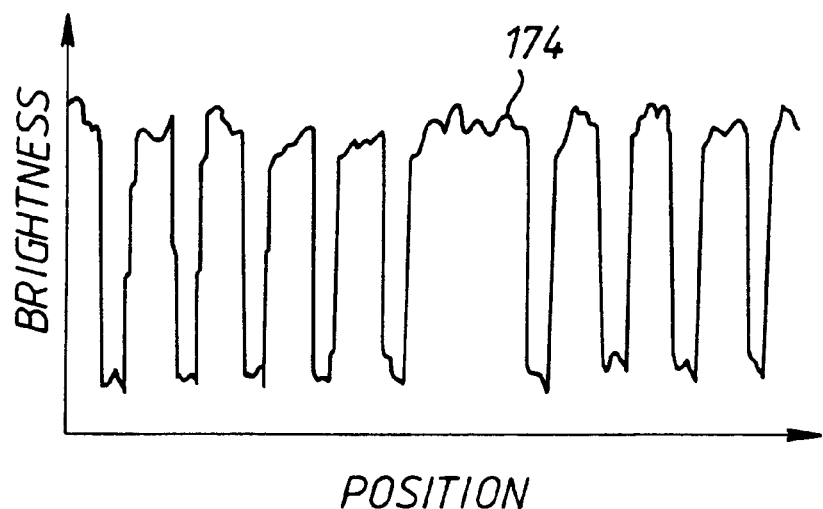
FIG. 28 is a graphical representation illustrating the brightness informations obtained along the transverse line of FIG. 26.

First of all, the brightness informations for each of the pixels obtained by the line senor 110 is divided into a plurality of lattices 172 each of which consists of a pixel matrix corresponding to the pitch of the holes 171, as can be seen in FIG. 27. In the dividing process, the lattice position designator 123 of FIG. 11 is utilized to designate the size of the lattice. The stain finder 90 will then process the brightness informations for the pixels contained in the respective lattice. In case where each of the holes 171 is found to have an irregular configuration, the shadow mask 170 shall be recognized as a defective one. The curve 174 of FIG. 28 illustrates the brightness informations obtained by the line sensor 110 along the transverse line 173 indicated in FIG. 26.

Figure 29:
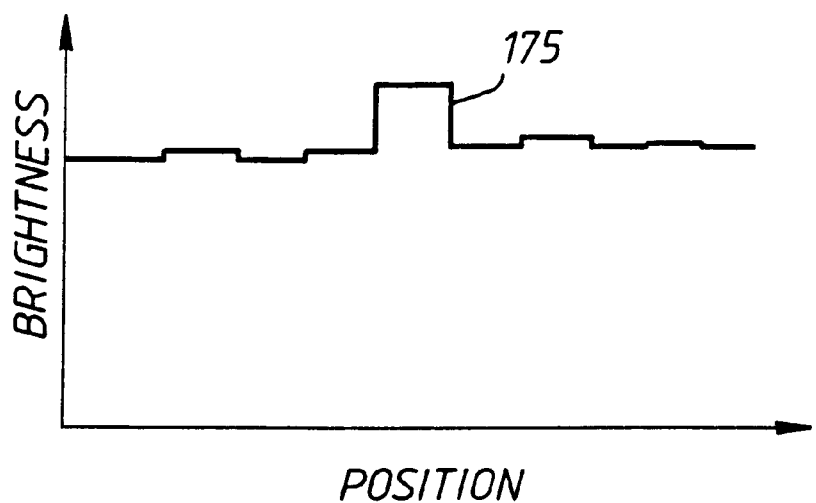
FIG. 29 is a view graphically representing the sum brightness values for a lattice corresponding to the transverse line of FIG. 26, in which each group of the sum brightness values are normalized with the greatest values.
Figure 30:
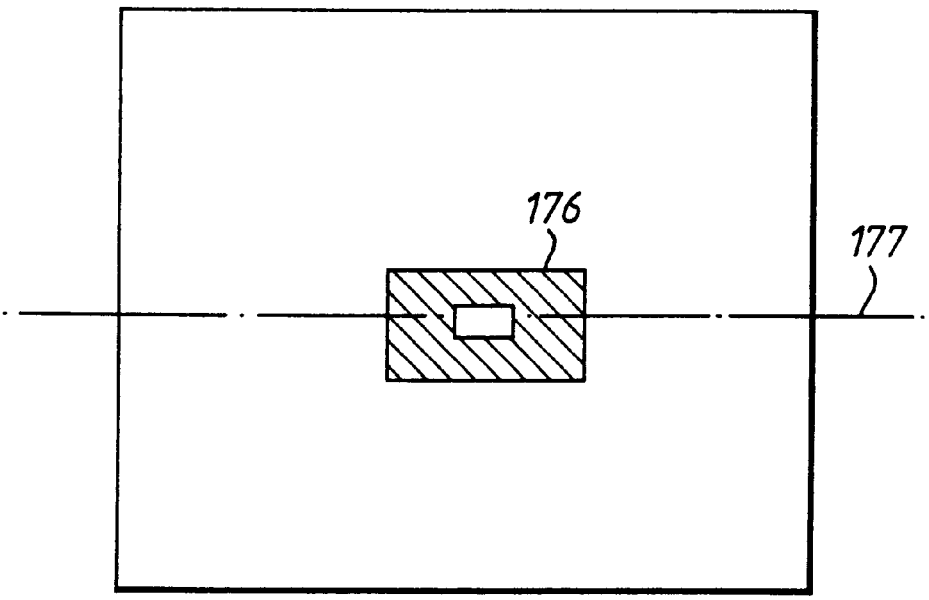
FIG. 30 is a top view illustrating the fluctuation magnitudes for each of the pixels in a normalized form.
Figure 31:
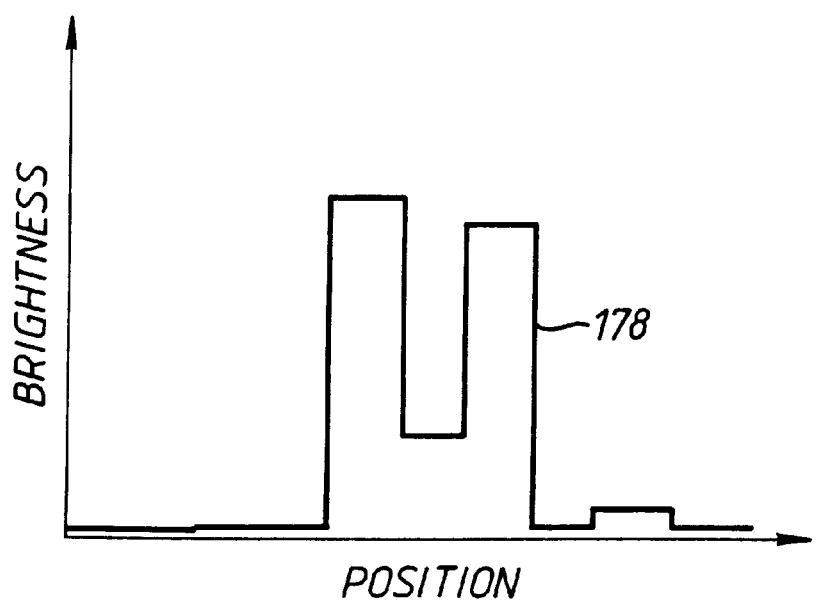
FIG. 31 is a graphical representation showing, in a normalized form, the fluctuation magnitudes for respective lattice corresponding to the transverse line of FIG. 26
Figure 39:
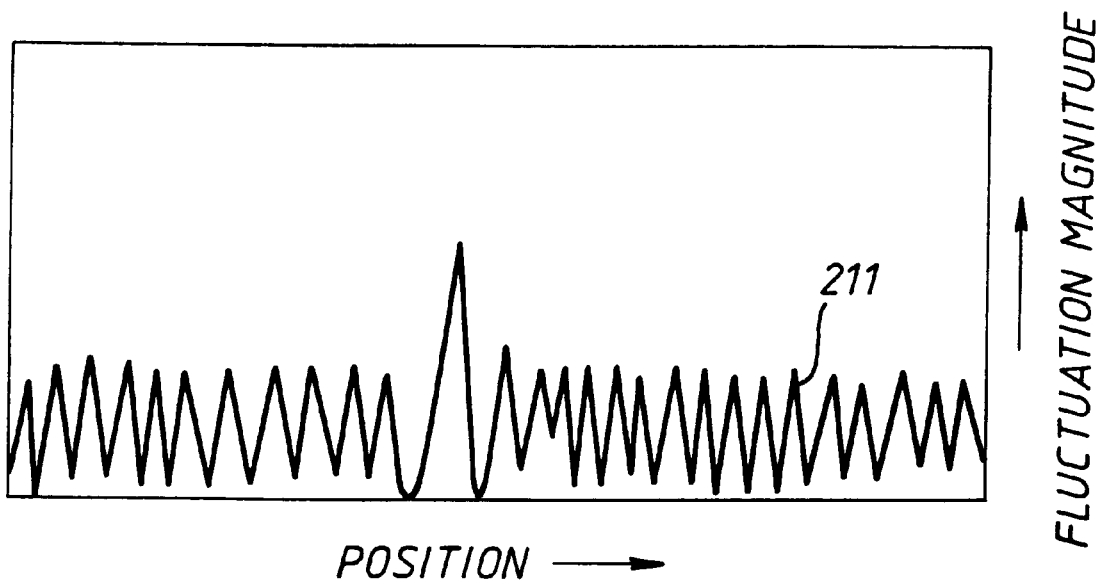
FIG. 39 graphically represents the mean fluctuation magnitudes obtained by way of adding the horizontal and vertical fluctuation magnitudes of the brightness informations shown in FIG. 38.

Such brightness informations is processed in the stain finder 90 and then displayed by the cathode ray tube 119 of the display 108, as shown in FIGS. 39 and 30. The curve 175 of FIG. 29 illustrates the stain by the greatest brightness informations, whereas the hatched zone 176 of FIG. 30 shows the stain as a plan view. Moreover, the curve 178 of FIG. 31 illustrates, in an emphasized condition, the brightness informations obtained along the transverse line 177 of FIG. 30. In other words, the brightness informations for the pixels obtained by the line sensor 110 are divided into a plurality of lattices in correspondence to the pitch of the penetration holes. Subsequently, the brightness informations for the pixels contained in the respective lattice are added to gain sum brightness values, thereby emphasizing the defect found in the object article. The defect is further emphasized by way of obtaining a horizontal fluctuation magnitude Hij and a perpendicular fluctuation magnitude $V_{ij}$ for the respective lattice through the use of a 3 row and 3 column matrix. Accordingly, it should become possible to detect ommission of a penetration hole as shown in FIG. 26.

Although the brightness information adder 105 in the above described embodiment divides the brightness informations into a lattice having a predetermined pixel matrix, e.g., 27 pixels in row and 44 pixels in column, this is not limitative in the present invention. If desired, the lattice may have 81 pixels in row and 44 pixel in column, for instance.

Even though the lattices are offset vertically and horizontally from the object article, they does not differ from one another as long as there is no defect in the object article. For this reason, it is not necessary to use a so-called "pattern matching technique" which accords the object article with the position of the respective lattice, thus making it possible to detect the defect with a high accuracy and in a convenient manner.

Figure 32:
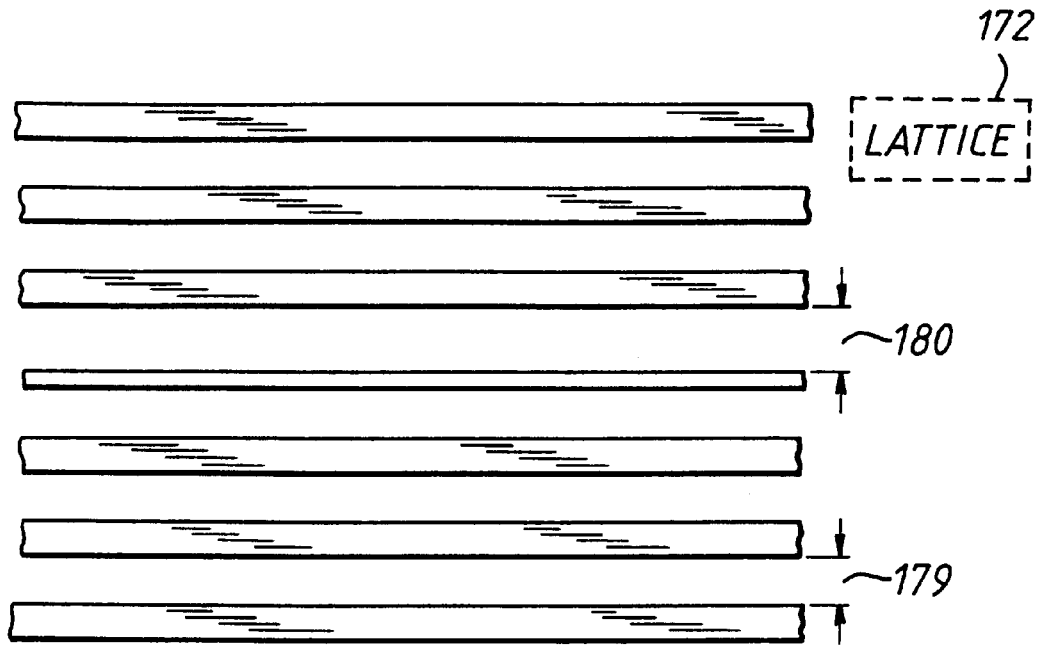
FIG. 32 shows an object article having a series of slits arranged in a predetermined spacing with each other.

While the method of finding a defect of the penetration holes formed through the CRT shadow mask was described in the above embodiment, it may well be possible to find a defect of the object article having a series of slits 179 with a given spacing, as illustrated in FIG. 32. In this case, the brightness information obtained by the line sensor 110 are divided into a lattice 172 shown by a broken line. By virtue of carrying out the same procedure as set forth above, it becomes possible to detect a defective slit 180 having a width broader than a reference width. In addition, detection may be made to find out a slit of narrow width, a slit of irregular shape or even a defect lying outside the slits.

Figure 33:
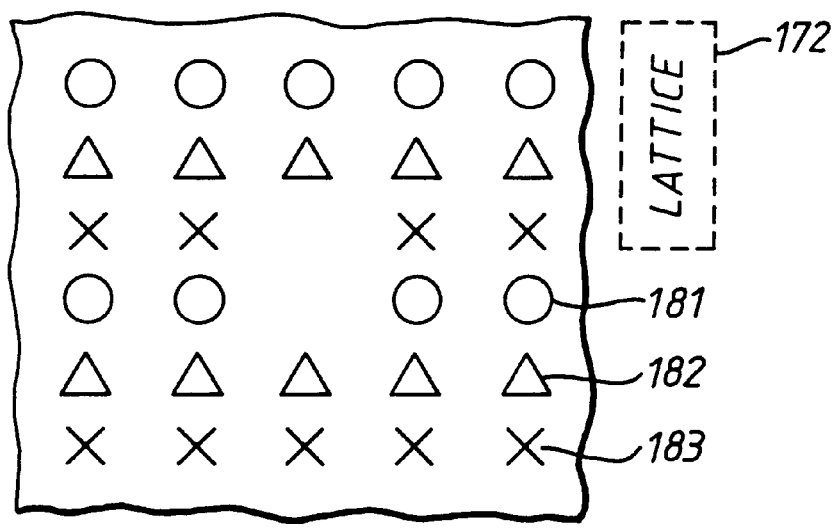
FIG. 33 shows and object article having different types of successive patterns.

As for the object article having various types of regularly arranged patterns as shown in FIG. 33, it would be possible to find out a defect in the same manner as explained above, i.e., by way of dividing the brightness informations obtained by the line sensor 110 into a lattice 172 shown in a broken line. Furthermore, detection of a discolored zone, an abnormal dyeing or an uneven area may be made with regard to the object article, e.g., LCD color filter, having a number of color segments. Other defect than abnormality in the holes of the shadow mask may also be detected by using the above disclosed technique. An area sensor may be used in place of the line sensor 110 if such need arises.

As is apparent from the foregoing description, in accordance with the first embodiment of the invention, the brightness informations for each of the pixels obtained by the line sensor are divided into a lattice having a given number of row and column matrixes or having a predetermined pitch. In the subsequent step, the brightness informations for the pixels in the respective lattice are added to gain sum brightness values, thereby emphasizing the stain present in the object article. The stain can be further emphasized by virtue of gaining horizontal and vertical fluctuation magnitudes in the sum brightness values. Detection of the stain depends on whether the horizontal and vertical fluctuation magnitudes exceed a predetermined reference value. This means that the detection may be performed with no dependency of direction and with a high accuracy.

Figure 34:
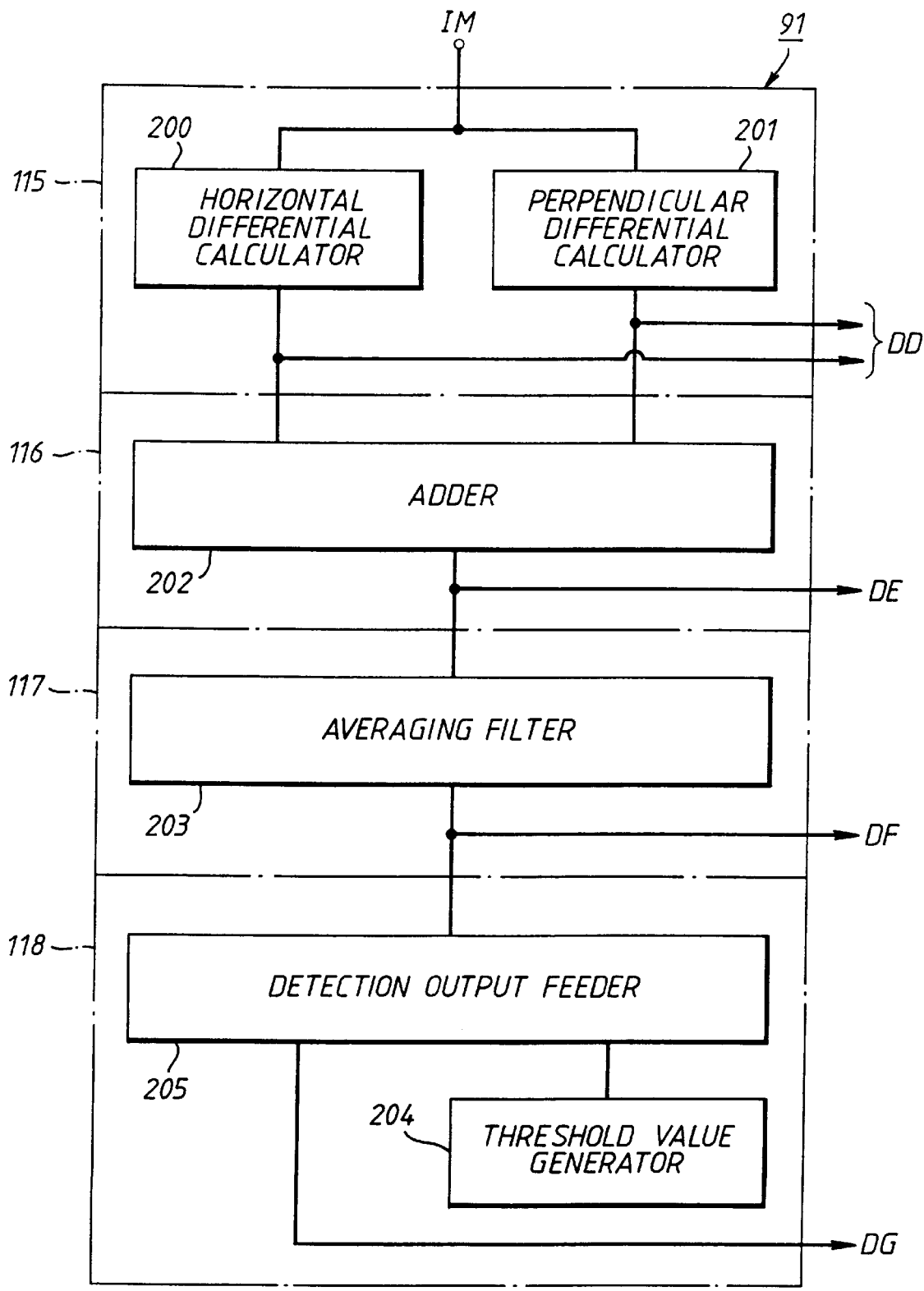
FIG. 34 is a block diagram showing a miniature defect finder of the surface irregularity inspection apparatus in accordance with the present invention.

A second embodiment of the invention will now be described in the following. FIG. 34 shows a modification of the defect finder 91 that constitutes the surface irregularity inspection apparatus as illustrated in FIG. 9. as can be seen in FIG. 34, the defect finder 91 comprises: a fluctuation magnitude calculator 115 adapted to receive the brightness informations from the line sensor 110 and having a horizontal differential calculator 200 and a perpendicular differential calculator 201; a fluctuation magnitude calculator 116 having an adder 202; a mean calculator 117 having an averaging filter 203; and a detector 118 having a threshold value generator 204 and a detection output feeder 205.

In the second embodiment, the line sensor 110 takes a picture of the object article such as a white film or a aluminium sheet used to make a beverage can, to thereby obtain brightness informations for a multiple number of two-dimensionally distributed pixels. As in the first embodiment described above, the horizontal and vertical differential calculator 200 and 201 serves to gain horizontal and vertical fluctuation magnitudes of the brightness informations through the use of a plurality of row and column matrixes, e.g., a first horizontal Sobel filter emphasizing a horizontal extending contour and a second vertical Sobel filter emphasizing a vertically extending contour. Other suitable filter, e.g., a filter of different coefficient or a filter of different matrix (2 rows by 2 columns or 3 rows by 1 column) may equally be used in place of the Sobel filter.

The adder 202 is adapted to add the horizontal and vertical fluctuation magnitudes, each of which is gained in the horizontal and vertical differential calculators 200 and 201. The averaging filter 203 functions to average the sum fluctuation magnitude gained by the adder 202 by use of a filter of FIG. 35 which takes the mean value of 9 (3 rows by 3 columns) fluctuation magnitudes as a mean value of the fluctuation magnitude for the center pixel, thus providing a mean fluctuation magnitude. The mean calculator 117 in the seconded embodiment can make use of other suitable filter of different coefficient, e.g., a filter having a coefficient of $\frac{2}{10}$ for the center pixel and a coefficient of $\frac{1}{10}$ for the peripheral pixels or a filter of different matrix, in place of the filter shown in FIG. 35.

The detector 118 serves to detect presence of the defect in case where the mean fluctuation magnitudes provided by the mean calculator 117 exceed a predetermined threshold value set by the threshold value generators 204. The display 108 is adapted to display the mean fluctuation magnitudes gained in the means calculator 117, the brightness informations for each of the pixels obtained by the area sensor, the horizontal and vertical fluctuation magnitudes gained in the fluctuation magnitude calculator and the horizontal and vertical sum fluctuation magnitudes gained in the fluctuation magnitude adder.

Figure 36:
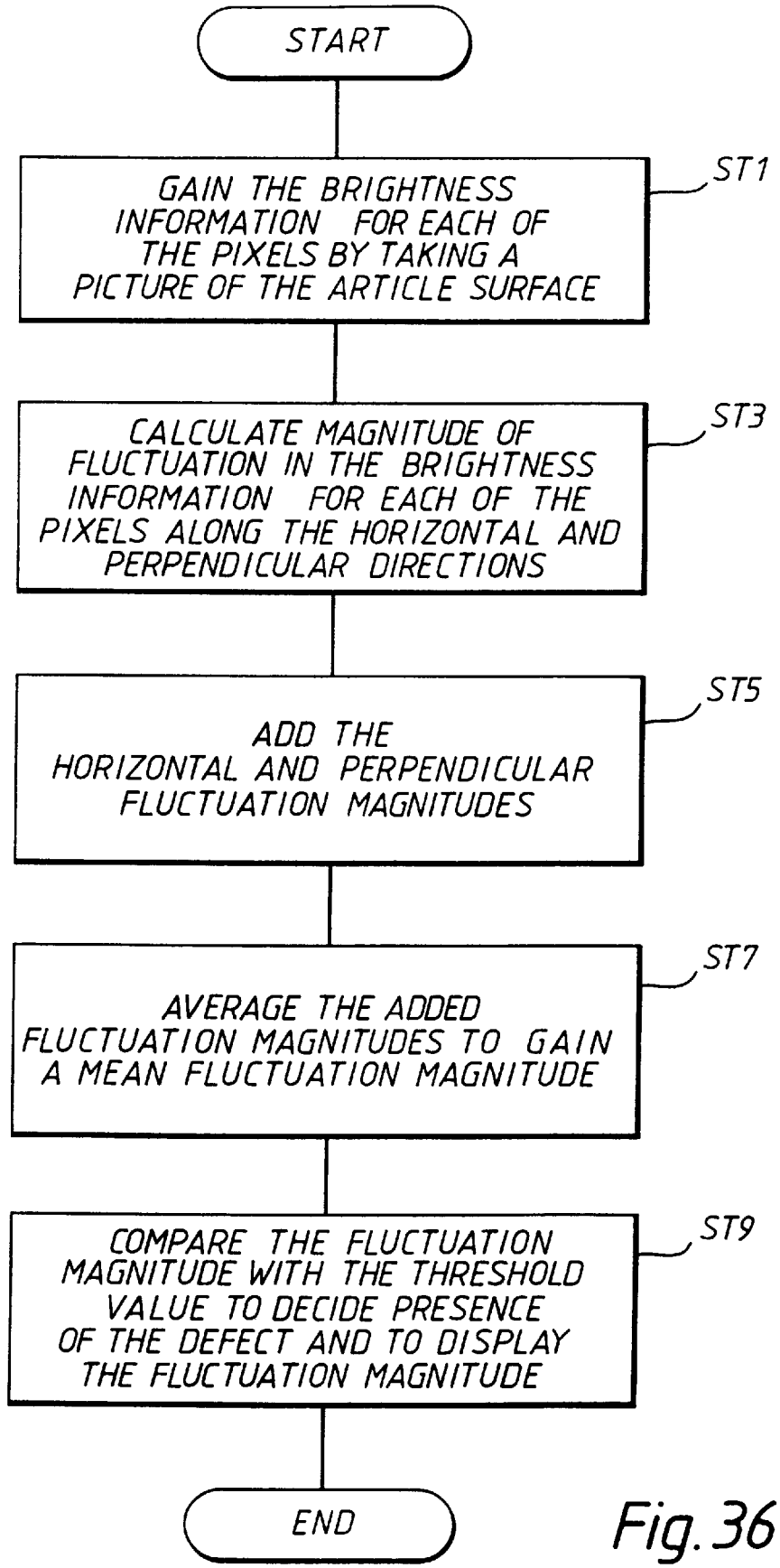
FIG. 36 is a flow chart illustrating operation of the surface irregularity inspection apparatus as depicted in FIG. 9.
Figure 37:
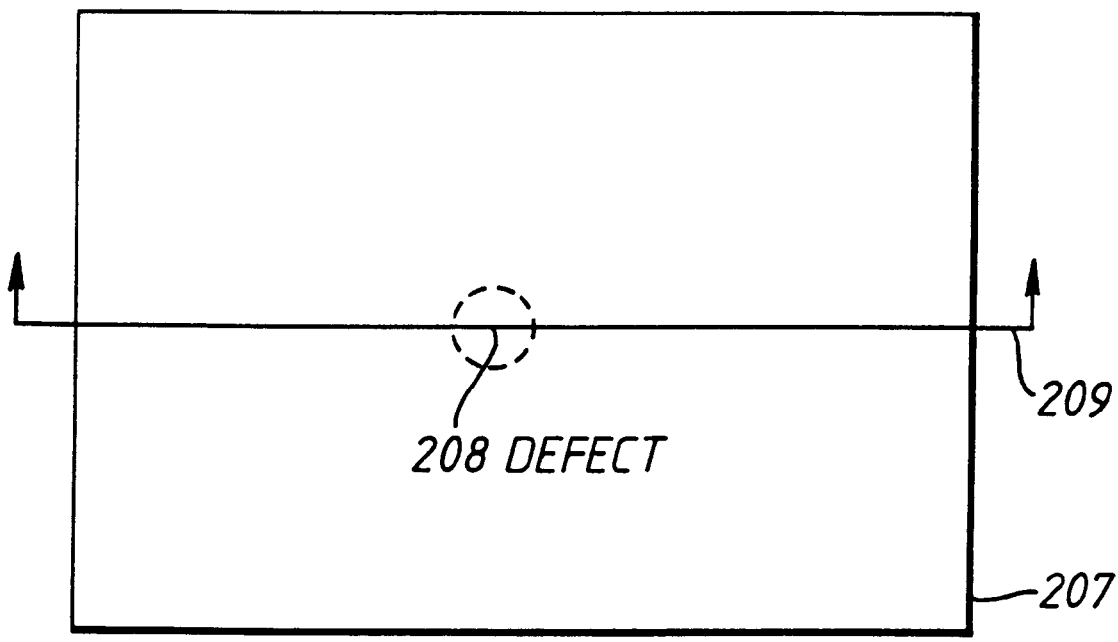
FIG. 37 shows a sheet-like film of white color having a microscopic foreign matter or defect at its center.

In the following, operation of the surface irregularity inspection apparatus in accordance with the second embodiment of the invention will be described with reference to the flow chart of FIG. 36. By way of example, it is assumed that detection is made to find a miniature defect 208 such as tiny flaw or foreign matter possibly present on the sheet-like white film 207 as shown in FIG. 37.

Figure 38:
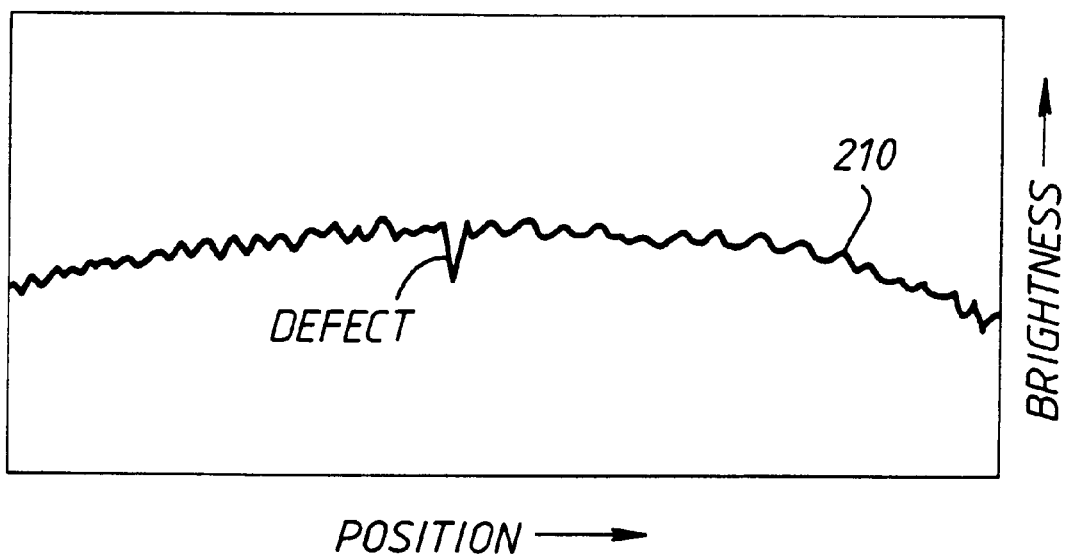
FIG. 38 is a view graphically representing the brightness information for the pixels which lie on a transverse line passing through the microscopic defect with the brightness informations including a shading and/or high frequency noise.

In the first instance, the line sensor takes a picture of the object article to obtain brightness informations for each of the pixels, the intensity of the respective brightness information subdivided into 256 levels ranging from 0 to 255 (Step 1). The curve 210 of FIG. 38 is a graphical representation of the brightness informations for the pixels lying along a transverse line 208 of FIG. 37.

Once the brightness informations are obtained in this manner, the fluctuation magnitude calculator 115 will calculate a horizontal fluctuation magnitude $H_{ij}$ and a vertical fluctuation magnitude $V_{ij}$ of the individual pixel by use of a 3 row and 3 column matrix (Step 3). For example, the horizontal and vertical fluctuation magnitudes $H_{ij}$ and $V_{ij}$ for one optional pixel $L_{ij}$ may be calculated through the use of a first horizontal Sobel filter shown in FIG. 17 and a second vertical Sobel filter shown in FIG. 19, based on the brightness informations for nine (3 rows by 3 columns) lattices around a reference pixel $L_{ij}$. The fluctuation magnitudes $H_{ij}$ and $V_{ij}$ can be given by the following equations:

$$H_{ij} = |L_{i-1,j-1} - 2L_{i,j-1} - L_{i+1,j-1} + L_{i-1,j+1} + 2L_{i,j+1} + L_{i+1,j+1}| \quad [4]$$

$$V_{ij} = |-L_{i-1,j-1} + L_{i-1,j-1} - 2L_{i-1,j} + 2L_{i+1,j} - L_{i-1,j+1} + L_{i+1,j+1}| \quad [5]$$

As soon as the fluctuation magnitudes $H_{ij}$ and $V_{ij}$ become known, the adder is operable to add them to thereby gain a sum fluctuation magnitude $T_{ij}$ (Step 5). The sum fluctuation magnitude along the transverse line 209 of FIG. 37 may be displayed on the display 108 as a curve 211 indicated in FIG. 39. As can be seen in FIG. 39, the defect still remains unclear due largely to the noise neighboring thereto.

Figure 35:
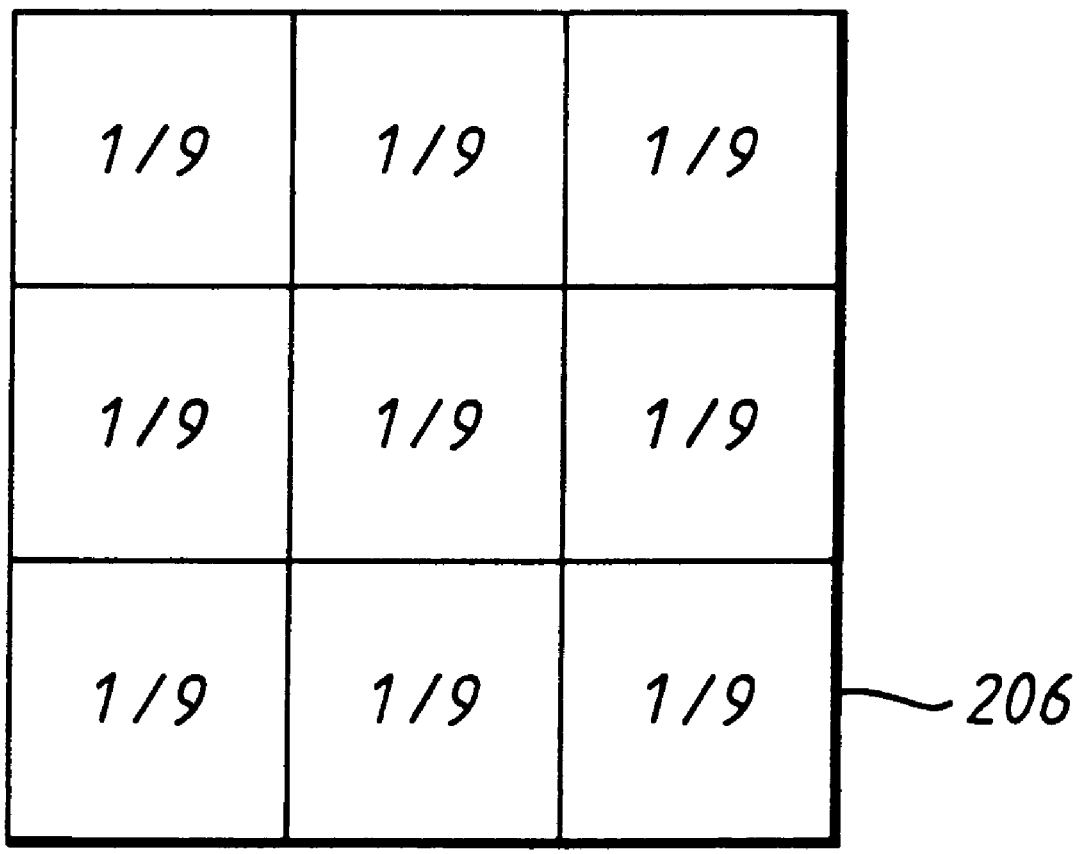
FIG. 35 shows a filter of 3 rows and 3 columns for gaining mean fluctuation magnitudes.

At the time when the sum fluctuation magnitudes are found for each of the pixels, the mean calculator 117 will average each of the sum fluctuation magnitudes through the use of the filter shown in FIG. 35 which is designed to equate a mean fluctuation magnitude of the centrally located pixel with the mean value of nine (3 rows by 3 columns) fluctuation magnitudes (Step 7). As an example, the mean fluctuation magnitude $A_{ij}$ of the pixel $L_{ij}$ may be expressed by the following equation:

$$A_{ij} = (T_{i-1,j-1} + T_{i,j-1} + T_{i+1,j-1} + T_{i-1,j} + \qquad [6]$$
$$T_{ij} + T_{i+1,j} + T_{i-1,j+1} + T_{i,j+1} + T_{i+1,j-1}) \times 1/9$$

wherein $T_{i-1, j-1}$ is a sum fluctuation magnitude of the pixel $L_{i-1, j-1}$; $T_{i, j-1}$ is a sum fluctuation magnitude of the pixel $L_{i, j-1}$; $T_{i+1, j-1}$ is a sum fluctuation magnitude of the pixel $L_{i+1, j-1}$; $T_{i-1, j}$ is a sum fluctuation magnitude of the pixel $L_{i-1, j}$; $T_{ij}$ is a sum fluctuation magnitude of the pixel $L_{ij}$; $T_{i+1, j}$ is a sum fluctuation magnitude of the pixel $L_{i+1, j}$; Ti-1, j+1 is a sum fluctuation magnitude of the pixel $L_{i-1, j+1}$; $T_{i, j+1}$ is a sum fluctuation magnitude of the pixel $L_{i, j+1}$; and $T_{i+1, j+1}$ is a sum fluctuation magnitude of the pixel $L_{i+1, j+1}$.

Figure 40:
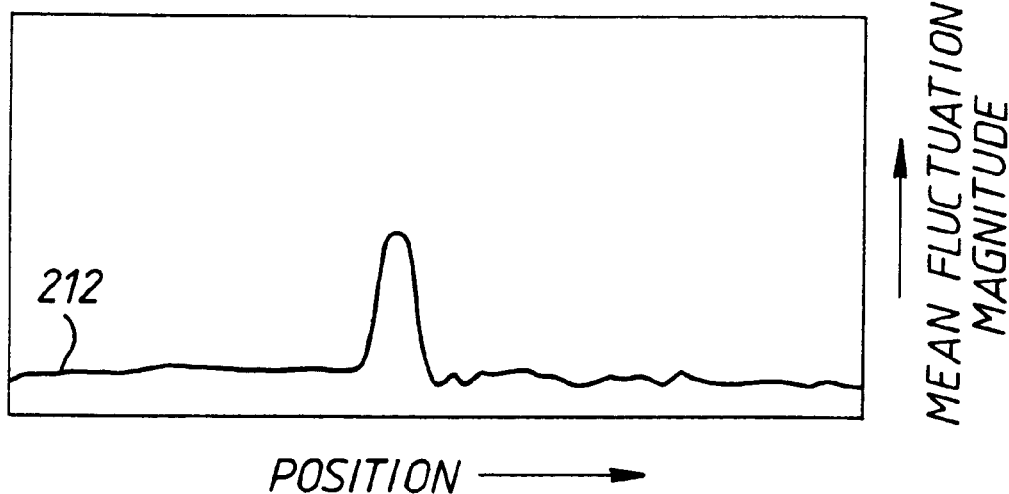
FIG. 40 is a graphical representation illustrating the mean fluctuation magnitudes for each of the pixels lying on the transverse line of FIG. 37.
Figure 41:
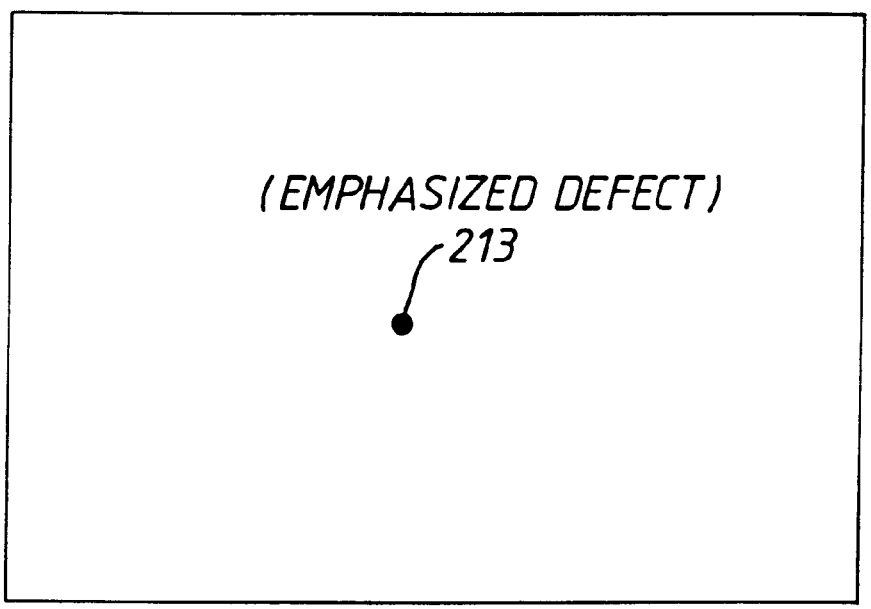
FIG. 41 shows the mean fluctuation magnitudes of FIG. 40 in a normalized form.

The detector 118 will then compare the mean fluctuation magnitude with a predetermined threshold value to detect presence of the defect in case where the former exceeds the latter. The mean fluctuation magnitudes for the pixels existing along the transverse line 209 of FIG. 37 can be displayed on the display 108 as a curve 212 as shown in FIG. 40. Alternatively, the mean fluctuation magnitude may be displayed in an emphasized fashion as illustrated by a think point 213 in FIG. 41 (Step 9).

Comparing the sum fluctuation magnitude of FIG. 40 reveals that the mean fluctuation magnitude does not accompany with any appreciable noise, thus highlightening the defect. For this reason, to ensure an accurate defect detection, it is preferable to use the mean fluctuation magnitude shown in FIG. 40 rather than the sum fluctuation magnitude of FIG. 39 gained by use of the first horizontal Sobel filter and the second vertical Sobel filter.

Use of the inventive surface irregularity inspection device stated hereinabove makes it possible to detect even a tiny defect slightly smaller or larger in size than a unit pixel, due to the significant reduction of the shading or high frequency noise entailed by the mean fluctuation magnitude. Although the contour of the object article may undesirably emphasized in the above detection process, it is possible to exclude the contour from the detection target by using a specially designed detector. Moreover, the defect finder 91 may employ a bandpass filter which has the ability to suppress creation of high frequency or low frequency noise.

An explained above in detail, the horizontal and vertical fluctuation magnitudes of the brightness informations obtained by the line sensor can be calculated through the use of a first horizontal Sobel filter and a second vertical Sobel filter. The horizontal and vertical fluctuation magnitudes are then added on a pixel basis to gain a sum fluctuation magnitude. The sum fluctuation magnitude is averaged by a filter that equates the mean value of nine (3 rows by 3 columns) sum fluctuation magnitudes with a mean fluctuation magnitude of the centrally located pixel. Employing such a mean fluctuation magnitude in the detection process insures an accurate detection of the miniature defect a bit smaller or larger in size than a unit pixel.

As is apparent from the foregoing description of the instant invention, the horizontal and vertical fluctuation magnitudes for N (m rows by n columns) brightness informations are calculated through the use of a first coefficient table emphasizing a horizontally extending contour and a second coefficient tables emphasizing a vertically extending contour. These horizontal and vertical fluctuation magnitudes are subsequently added together to gain sum fluctuation magnitudes for each of the pixels. An averaging step is carried out to gain mean fluctuation magnitudes by using a m row and n column table which is adapted to average the sum fluctuation magnitudes on the basis of N (m rows by n columns) sum fluctuation magnitudes. The mean fluctuation magnitudes are advantageously used to find out the miniature defect appearing on the object article.

While the present invention has been shown and described with reference to certain preferred embodiments, it should be apparent to those skilled in the art that may changes and modifications may be made without departing from the spirit and scope of the invention as defined in the claims.

What is claimed is:

1. A method of inspecting a surface of an object for irregularities which are unclearly different and have a minor difference of brightness from the surface, which comprises the steps of:

obtaining a brightness value for a plurality of pixels by generating an image of said object;

adding brightness values by dividing the brightness obtained from each of said pixels in the brightness value obtaining step into a plurality of brightness value lattices having pixels of p rows and q columns, and adding the brightness value of each pixel in each brightness lattice, to determine a sum brightness value for each of said brightness lattices;

dividing along a horizontal direction by dividing the sum brightness value for each of said brightness value lattices obtained in said brightness adding step into lattices having a sum brightness value of m rows by n columns; and multiplying n numbers of sum brightness values belonging to each of m rows by a first coefficient which is previously determined for each location of said sum brightness values in said lattices having the sum brightness values, to obtain a multiplied result for each of said lattices having the sum brightness values;

multiplying along a vertical direction by multiplying m numbers of sum brightness values belonging to each of n columns by a second coefficient which is previously determined for each location of said sum brightness values in said lattices having the sum brightness values, to obtain a multiplied result for each of said lattices having the sum brightness values;

calculating magnitudes of fluctuation along a horizontal direction by adding the multiplied result in each lattice having the sum brightness value obtained in the multiplying step along the horizontal direction to determine magnitudes of fluctuation of the brightness along the horizontal direction;

calculating magnitudes of fluctuation along a vertical direction by adding the multiplied result in each lattice having the sum brightness value obtained in said multiplying step along the vertical direction to determine magnitudes of fluctuation of the brightness along the vertical direction; and repeatedly calculating magnitudes of fluctuation by repeating the step of multiplying along the horizontal direction, the step of multiplying along the vertical direction, the step of calculating magnitudes of fluctuation along the horizontal direction and the step of calculating magnitudes of fluctuation along the vertical direction with a shift in horizontal and vertical directions.

2. The method according to claim 1 further comprising a step of comparing said magnitudes of fluctuation along the horizontal direction and a threshold value along the horizontal direction with said magnitudes of fluctuation along the vertical direction and a threshold value along the vertical direction.

3. The method according to claim 1 further comprising a step of adding said magnitudes of fluctuation along the horizontal direction and said magnitudes of fluctuation along the vertical direction, and a step of comparing the added magnitudes of fluctuation with a threshold value.

4. The method according to any of claims 1–3, wherein said object has a monochrome patternless surface, and areas with irregularities with a slightly different color on the surface are inspected.

5. The method according to any of claims 1–3, wherein said object has areas with irregularities having a slightly different thickness from a prescribed thickness of said object.

6. The method according to any of claims 1–3, wherein said object has a surface of a shape arranged at a predetermined pitch, and areas with irregularities having a pitch slightly different from said pitch is inspected.

7. The method according to any of claims 1–3, wherein said object is a nonwoven fabric.

8. The method according to any of claims 1–3, wherein said object is a sheet of paper.

9. A device for inspecting a surface of an object for irregularities which are unclearly different and have minor difference of brightness from the surface, comprising:

an input device including a sensor for generating an image of the surface of said object, a lighting device for lighting the surface of said object, and a position detector for detecting the image position on the surface of said object;

an irregularity detecting device including an irregularity information adder, a brightness fluctuation magnitude detector, and an irregularity detector; and a displaying section including a display for displaying an output signal from said irregularity detector and a printer for printing said output signal;

said irregularity information adder including a pixel lattice divider for dividing brightness information for each pixel obtained by said sensor into rows and columns of pixels, a pixel lattice position designator, and a brightness information adder for adding the brightness information of each pixel in said pixel lattice to obtain a sum brightness value of each pixel lattice;

said brightness fluctuation magnitude detector including a separator for separating a signal from said brightness information adder into horizontal and vertical directions of the sum brightness value, a multiplier for multiplying said separated signal in said horizontal direction by a first coefficient and said separator signal in the vertical direction by second coefficient to obtain a multiplied result and horizontal and vertical fluctuation magnitude calculators for calculating magnitudes of fluctuation of the sum brightness values, between said pixel lattices along horizontal and vertical directions separated by said separator by adding said multiplied results;

said irregularity detector including a threshold value generator and a comparator for comparing a threshold value generated by said threshold value generator, the magnitudes of fluctuation calculated by said horizontal and vertical fluctuation magnitude calculators, and a threshold value generated by said threshold value generator.

10. The device according to claim 9, wherein said irregularity detector includes an adder for adding the magnitudes of fluctuation calculated by said horizontal and vertical fluctuation magnitude calculators, and compares an output signal from said adder and a threshold value generated from said threshold value generator by said comparator.

11. The device according to any of claims 9 or 10, wherein said irregularity detector includes a labeling output feeder and a center position output feeder for receiving an output signal from said comparator, said labeling output feeder outputs an area of irregularity, and said center position output feeder outputs a plane center position coordinator of irregularities.

\* \* \* \* \*